United States Patent [19]

Eastman et al.

[11] Patent Number: 6,103,470
[45] Date of Patent: *Aug. 15, 2000

[54] PLASMID FOR DELIVERY OF NUCLEIC ACIDS TO CELLS AND METHODS OF USE

[75] Inventors: Eric M. Eastman, Houston; Ross H. Durland, The Woodlands, both of Tex.

[73] Assignee: Genemedicine, Inc., The Woodlands, Tex.

[ * ] Notice: This patent is subject to a terminal disclaimer.

[21] Appl. No.: 09/001,770

[22] Filed: Dec. 31, 1997

Related U.S. Application Data

[63] Continuation of application No. 08/484,723, Jun. 7, 1995, Pat. No. 5,763,270.

[51] Int. Cl.⁷ .............................. C12Q 1/68; C12N 15/00
[52] U.S. Cl. ............................................. 435/6; 435/320.1
[58] Field of Search ........................ 435/320.1, 6; 514/44

[56] References Cited

U.S. PATENT DOCUMENTS 5,763,270  6/1998  Eastman ................................ 435/320.1

FOREIGN PATENT DOCUMENTS

| | | |
|---|---|---|
| 0 345 615 | 12/1989 | European Pat. Off. . |
| WO 93/11229 | 6/1993 | WIPO . |
| WO 94/29468 | 12/1994 | WIPO . |

OTHER PUBLICATIONS

Aslandis et al., "Regulatory Elements of the Raffinose Operon: Nucleotide Sequences of Operator and Repressor Genes," *J. Bacteriol.* 172:2178–2180 (1990).

Barker et al., "Sequence and Properties of Operator Mutations in the bio Operon of *Escherichia Coli*" *Gene* 13:56–102 (1981).

Bautista et al., "Insertional Mutagenesis Using a Synthetic lac Operator," Gene 82:201–208 (1989).

Benner–Luger et al., "The mglB Sequence of *Salmonella Typhimurium* LT2; Promoter Analysis by Gene Fusions and Evidence for a Divergently Oriented Gene Coding for mgl Repressor," Mol. Gen. Genet. 214:579–587 (1988).

Bentley et al., "Plasmid–encoded Protein: The Principal Factor in the 'Metabolic Burden' Associated with Recombinant Bacteria," Biotechnology and Bioengineering 35:668–681 (1990).

Brosius, J., "Toxicity of an Overproduced Foreign Gene Product in *Escherichia Coli* and its Use in Plasmid Vectors for the Selection of Transcription Terminators," Gene 27:161–172 (1984).

Brosius, J. et al., "Regulation of Ribosomal RNA Promoters with a Synthetic lac Operator," Proc. Natl. Acad. Sci. USA 81:6929–6933 (1984).

Brykun et al., "Cloning of *Escherichia Coli* Uridine Phosphorylase Gene (UDP): Location of Structural and Regulatory Regions in the Cloned Fragment and Identification of Corresponding Protein," Mol Gen. Mikrobiol. Virusol. 6:7–11 (1990).

Brykun et al., "Cloning the *Escherichia Coli* Uridine Phosphorylase Gene (UDP): and Its Expression in the Recombinant Plasmids," Genetika 25:1717–1724 (1989).

Chen et al., "Construction and Characterization of a Novel Cross–regulation System for Regulating Cloned Gene Expression in *Escherichia Coli*", Gene 130:15–22 (1993).

Cornet et al., "Plasmid psC101 Harbors a Recombination Site, psi, which is able to Resolve Plasmid Multimers and to Substitute for the Analogous Chromosomal *Escherichia Coli* Site dif," J. Bacteriology 176:3188–3195 (1994).

Danner, D., "The lac Operator as a Phenotype Label for DNA Fragments Cloned in *Escherichia Coli*," Gene 44:193–199 (1986).

Diederich et al., "New Cloning Vectors for Integration into the λ Attachment Site attB c the *Escherichia Coli* Chromosome," Plasmid 28:14–24 (1992.

Eberl et al., "Analysis of the Multimer Resolution System Encoded by the parCBA Operon of Broad Host–range Plasmid RP4," Molecular Microbiology 12:131–141 (1994).

Engels et al., "Inactivation of the transcriptional–dependent inhibition of plasmid replication: A selection method for cloning large DNA fragments," BioTechniques 14:324–325 (1993).

Fitzwater et al., "Conditional high copy number ColE1 mutants: resistance to RNA1 inhibition in vivo and in vitro," EMBO J 7:3289–3297 (1988).

Fritz et al., "Characterization of two mutations in *Escherichia coli* gene inactivating the second galactose operator and comparatively studies of repressor binding," EMBO J. 2:2129–2135 (1983).

Fujita et al., "Identification and nucleotide sequence of the promoter region of the *Bacillus Subtilis* Gluconate Operon," Nucleic Acids Research 14:1237–1252 (1986).

Ghersa et al., "Commonly used cat reporter vectors contain a cAMP–inducible, cryptic enhancer that co–operates with NF–$_k$B–sites," Gene 151:331–332 (1994).

Giza et al., "A self–inducing runaway–replication plasmid expression system utilizing the Rop protein," Gene 78:73–84 (1989).

Hammer et al., "DNA specificity of *Escherichia coli* deoP1 Operator–DeoR Repressor Recognition," Mol. Gen. Genet. 237:129–133 (1993).

Hiraga, "Chromosome and plasmid partition in *Escherichia Coli*," Ann. Rev. Biochem. 61:283–306 (1992).

Huong et al., "Molecular cloning and physical and functional characterization of the *salmonella typhimurium* and *salmonella typi* galactose utilization operons," J. Bacteriology 172:4392–4398 (1990).

(List continued on next page.)

*Primary Examiner*—Eggerton A. Campbell
*Attorney, Agent, or Firm*—Lyon & Lyon LLP

[57] ABSTRACT

This invention relates to plasmid constructs useful for non-viral human gene therapy. The plasmid constructs incorporate plasmid elements for achieving high copy number, avoiding plasmid instability an providing a plasmid selection process. These constructs can be used to deliver nucleic acids to cells in vehicles which are compatible with human therapeutic use.

30 Claims, 14 Drawing Sheets

OTHER PUBLICATIONS

Jensen et al., "Partitioning of plasmid R1: the ParA Operon is Autoregulated by ParR and its Transcription is highly stimulated by a downstream activating element," J. Mol. Biol. 236:1299–1309 (1994).

Kilstrup et al., "Nucleotide sequence of the carA gene and regulation of the carAB operon in *Salmonella Typhirium*," Eur. J. Biochem 176:421–429 (1988).

Kushner et al., "Eukaryotic Regulatory Elements lurking in plasmid DNA: the activator protein–1 site in pUC," Molecular Endocrinology 8:405–407 (1994).

Latour et al., "Regulation of in vitro expression of *Escherichia coli* frd operon: alanine and Fnr represent positive and negative control elements," Nucleic Acids Research 16:6339–6352 (1988).

Leite et al., "Negative effect of cis–acting pBR322 element on adenovirus E1a gene expression," Gene 82:351–356 (1989).

Linder et al., "Regulation of xylanolytic enzymes in *Bacillus Subtilis*," Microbiology 140:753–757 (1994).

Lusky et al., "Inhibition of SV40 replication in simian cells by specific pBR322 DNA sequences," Nature 293:79–81 (1981).

Lutz et al., "Syrinx 2A: An improved λ phage vector designed for screening DNA libraries by recombination in vivo," Proc. Natl. Acad. Sci. USA 84:4379–4383 (1987).

Mata–Gilsinger et al., "Characterization of the operator siters of the EXU regulon in *Escherichia coli* K–12 by operator–constitutive mutations and repressor titration," Genetics 105:829–842 (1983).

Naik et al., "Use of site–directed mutagenesis to identify an upstream regulatory sequence of sodA gene of *Escherichia coli* K–12," Proc. Natl. Acad. Sci. USA 87:2618–2622 (1990) (39).

Oskouian et al., "Cloning and characterization of the repressor gene of the *Staphylococcus aureus* lactose operon," J. Bacteriology 169:5459–5465 (1987).

Osuna et al., "Identification of the hutUH operator (hutUo) from *Klebsiella aerogenes* by DNA deletion analysis," J. Bacteriology 176:5525–5529 (1994).

Park et al., "Two–stage fermentation with bacteriophate λ as an expression vector in *Escherichia coli*," Biotechnology and Bioengineering 37:297–302 (1991).

Peretti et al., "Simulations of host–plasmid interactions in *Escherichia coli*: copy number, promoter strength, and ribosome binding site strength effects on metabolic activity and plasmid gene expression," Biotechnology and Bioengineering 29:316–328 (1987).

Peterson et al., "Context–dependent gene expression: cis––acting negative effects of specific procaryotic plasmid sequences on Eucaryotic genes," Mol. Cell. Biol. 7:1563–1567 (1987).

Porter et al., "Use of *Escherichia Coli* SSB gene to prevent bioreactor takeover by plasmidless cells," Biotechnology 8:47–51 (1990).

Recombinant DNA Advisory Committee Data Management Report, Human Gene Therapy 6:535–548 (1994).

Salmaron et al., "Interaction between transcriptional activator protein LAC9 and negative regulatory protein GAL80," Mol. Cell. Biol. 9:2950–2956 (1989).

Sambrook et al., Molecular Cloning: A Laboratory Manual, $2^{nd}$ Ed. 1989, (Table of Contents).

Simons et al., Possible ideal lac operator: *Escherichia coli* lac operator–like sequences from eukaryotic genomes lack the central G–C pair, Proc. Natl. Acad. Sci. USA 81:1624–1628 (1984).

Smith, "Regulatory considerations for nucleic acid vaccines," Vaccine 12(16):1515–1519 (1994).

Sogaard–Andersen et al., "Tandem DNA bound cAMP–CRP complexes are required for transcriptional repression of the deoP2 promoter by the CytR repressor in *Escherichia coli*," Mol. Microbiol. 4:1595–1601 (1990).

Stragier et al., "Regulatory Pattern of the *Escherichia coli* lysA gene: Expression of chromosomal lysA–lacZ fusions," J. Bacteriology 156:1198–1203 (1983).

Summers et al., "Multimer resolution systems of ColE1 and ColK: localization of the crossover site," Mol. Gen. Genet. 201:334–338 (1985).

Suzuki et al., An Introduction to Genetic Analysis, 399–405 (1989).

Tully et al., "pBR322 contains glucocorticoid regulatory element DNA consensus sequences," Biochem. Biophys. Res. Commun. 144:1–10 (1987).

Uhlin et al., "A runaway–replication mutant of plasmid R1drd–19:temperature–dependent loss of copy number control," Mol. Gen. Genet. 165:167–179 (1978).

Villarreal et al., "Comparison of the transient late region expression of SV40 DNA and SV40 based shuttle vectors: development of a new shuttle vector that is efficiently expressed," J. Mol. Appl. Genet. 3:62–71 (1985).

Virolle et al., "Sequences involved in growth–phase–dependent expression and glucose repression of a streptomyces α–amylase gene," Microbiology 140:1059–1067 (1994) (39).

Williams et al., "Active partitioning of bacterial plasmids," J. Gen. Microbiol. 138:1–16 (1992).

Windass et al., "Abberant immunity behaviour of hybrid λimm$^{21}$ phages containing the DNA of ColE1–type plasmids," Mol. Gen. Genet. 172:329–337 (1979).

Wray et al., "Identification of repressor binding sites controlling expression of tetracycline resistance encoded by Tn10," Bacteriology 156:1188–1191 (1983).

Yoder et al., "Procaryotic genomic DNA inhibits mammalian cell transformation," Mol. Cell. Biol. 3:956–959 (1983).

PLASMID FOR DELIVERY OF NUCLEIC ACIDS TO CELLS AND METHODS OF USE

This application is a continuation of Eric M. Eastman et al., U.S. Ser. No. 08/484,723, filed Jun. 7, 1995, U.S. Pat. No. 5,763,270 entitled "Plasmid For Delivery of Nucleic Acids to Cells and Methods of Use" which is incorporated herein by reference in its entirety including any drawings.

BACKGROUND OF THE INVENTION

This invention relates to plasmid constructs for delivery of therapeutic nucleic acids to cells. In addition, this invention relates to methods of using those constructs as well as methods for selection of desired plasmids. Such constructs and methods are useful in human gene therapy.

Plasmids are an essential element in genetic engineering and gene therapy. Plasmids are circular DNA molecules that can be introduced or transfected into bacterial cells by transformation which replicate autonomously in the cell. They offer several advantages as vectors, the most important of which is the ability to confer antibiotic resistance to the host cell. This allows direct selection for cells that receive and maintain recombinant DNA plasmids. Plasmids also allow the amplification of cloned DNA. Some plasmids are present in 20 to 50 copies during cell growth, and after the arrest of protein synthesis, as many as 1000 copies per cell of a plasmid can be generated. (Suzuki et al., *Genetic Analysis*, p. 404, (1989).)

Current non-viral approaches to human gene therapy require that a potential therapeutic gene be cloned onto plasmids. Large quantities of a bacterial host harboring the plasmid may be fermented and the plasmid DNA may be purified for subsequent use. Current human clinical trials using plasmids utilize this approach. (Recombinant DNA Advisory Committee Data Management Report, December, 1994, *Human Gene Therapy* 6:535–548). Studies normally focus on the therapeutic gene and the elements that control its expression in the patient when designing and constructing gene therapy plasmids. Generally, therapeutic genes and regulatory elements are simply inserted into existing cloning vectors that are convenient and readily available.

Plasmid design and construction utilizes several key factors. First, plasmid replication origins determine plasmid copy number, which affects production yields. Plasmids that replicate to higher copy number can increase plasmid yield from a given volume of culture, but excessive copy number can be deleterious to the bacteria and lead to undesirable effects (Fitzwater, et al., *Embo J.* 7:3289–3297 (1988); Uhlin, et al., *Mol. Gen. Genet.* 165:167–179 (1979)). Artificially constructed plasmids are sometimes unstably maintained, leading to accumulation of plasmid-free cells and reduced production yields.

To overcome this, genes that code for antibiotic resistance phenotype are included on the plasmid antibiotics are often added to kill or inhibit plasmid-free cells. Most general purpose cloning vectors contain ampicillin resistance (β-lactamase, or bla) genes. Use of ampicillin can be problematic because of the potential for residual antibiotic in the purified DNA, which can cause an allergic reaction in a treated patient. In addition, β-lactam antibiotics are clinically important for disease treatment. When plasmid containing antibiotic resistant genes are used, the potential exists for the transfer of antibiotic resistance genes to a potential pathogen.

Other studies have used the neo gene which is derived from the bacterial transposon TnS. The neo gene encodes resistance to kanamycin and neomycin (Smith, *Vaccine* 12:1515–1519 (1994)). This gene has been used in a number of gene therapy studies, including several human clinical trials (Recombinant DNA Advisory Committee Data Management Report, December, 1994, *Human Gene Therapy* 6:535–548). Due to the mechanism by which resistance is imparted, residual antibiotic and transmission of the gene to potential pathogens may be of a problem than for β-lactams.

Several studies have reviewed alternatives to antibiotic selection. One study made use of genes that are essential to growth of the *E. coli* host, such as the ssb gene, encoding the DNA single strand binding protein (Porter, et al., *Bio/Technology* 8:47–51 (1990)). This gene was cloned onto plasmids and used as a selectable marker in host strains lacking the chromosomal ssb gene. Because the product of the ssb gene is essential for growth, plasmid-free cells are nonviable.

A second group of studies reviewed the use of suppressor tRNA genes (Lutz, et al., *Proc. Natl. Acad. Sci. USA* 84:4379–4383 (1987) and Villarreal and Soo, *J. Mol. Appl. Genet.* 3:62–71 (1985)). One or more antibiotic resistance genes were modified to contain nonsense (stop) codons. These genes were then introduced into the host chromosome. A plasmid was then modified to contain an appropriate suppressor tRNA capable of suppressing the nonsense mutations in the antibiotic resistance genes. Introduction of the plasmid into the modified host suppresses the mutations in the resistance genes, rendering the cells able to grow in the presence of antibiotics.

Other plasmid elements which have been studied include partition elements. Such elements help stabilize plasmid maintenance independent of antibiotic selection (Hiraga, *Ann Rev. Biochem.* 61:283–306 (1992); Williams and Thomas, *J. Gen. Microbiol.* 138:1–16 (1992)). In addition, other elements promote monomerization of the plasmid. Some plasmids are prone to forming dimers, trimers and higher multimers that can reduce yield and interfere with maintenance, as well as generating a more complicated product profile. Multimer resolution elements have been employed to promote monomerization of plasmids (Eberl, et al., *Mol. Microbiol.* 12:131–141 (1994); Cornet, et al., *J. Bacteriol.* 176:3188–3195 (1994); and Summers, et al., *Mol. Gen. Genet.* 201: 334–338 (1985)).

In addition to elements that affect the behavior of the plasmid in the host bacteria, such as *E. coli*, plasmid vectors have also been shown to affect transfection and expression in eukaryotic cells. Certain plasmid sequences have been shown to reduce expression of eukaryotic genes in eukaryotic cells when carried in cis (Peterson, et al., *Mol. Cell. Biol.* 7:1563–1567 (1987); Yoder and Ganesan, *Mol. Cell. Biol.* 3:956–959 (1983); Lusky and Botchan, *Nature* 293:79–81 (1981); and Leite, et al., *Gene* 82:351–356 (1989)). Plasmid sequences also have been shown to fortuitously contain binding sites for transcriptional control proteins (Ghersa, et al., *Gene* 151:331–332 (1994); Tully and Cidlowski, *Biochem. Biophys. Res. Comm.* 144:1–10 (1987); and Kushner, et al., *Mol. Endocrinol.* 8:405–407 (1994)). This can cause inappropriate levels of gene expression in treated patients. In many cases, it is difficult or nearly impossible to predict when such unintended interactions will occur, unless empirical evaluation reveals the unexpected effects.

SUMMARY OF THE INVENTION

Applicant has determined that it is useful to construct plasmids based upon particular plasmid elements to achieve various goals for use in nonviral gene therapy. Specifically, these elements cause regulated high copy number when replicated in bacteria, avoid potential causes of plasmid instability and provide a means for plasmid selection compatible with human therapeutic use. In addition, all elements of the plasmids may be easily removed or replaced as needed. These plasmids are useful in facilitating nonviral human gene therapy. These plasmids can be used to treat diseases by targeting the plasmids accordingly. These plasmids can also be used to create transgenic animals.

Taking advantage of the above elements as used with plasmids, the present invention features use of these plasmids in operator selection methods. In particular, the present invention permits the use of antibiotics to select plasmid maintenance based on the presence of a small (about 20 bp) selectable element in the plasmid rather than the plasmid having to contain the antibiotic resistance gene itself. Such an element reduces or eliminates potential concerns about antibiotic resistant genes cloned on plasmids, but retains the advantages offered by antibiotics, i.e., low cost, efficient inhibition of the production of plasmid-free cells and ease of use. Operator selection reduces concerns that the antibiotic resistance gene may be a potential safety hazard when transferred to human patients, either directly or by increasing the possibility of generating antibiotic resistant pathogens. Operator selection also reduces or eliminates the potential metabolic energy cost to the host cell associated with expression of an antibiotic resistance gene present on a high copy number plasmid.

The ability of the above plasmids to efficiently direct nucleic acid to a cell allows the plasmids to be used for treating numerous diseases. Such treatment depends in part on the therapeutic gene within the nucleic acid cassettes, i.e., the nucleic acid carrying the therapeutic gene. Furthermore, the above plasmids can also be used to transform cells to produce particular proteins, polypeptides, and RNA, as well as used to create immune responses. In a first aspect, the present invention features a plasmid for the delivery of a nucleic acid sequence to cells. Such delivery includes production of plasmid nucleic acid sequences in bacteria, e.g., E. coli. The plasmid includes: (1) a 5' flanking region which contains defined nucleic acid sequences that regulate plasmid copy number; (2) a 3' flanking region which contains defined nucleic acid sequences that regulate selection for plasmid-bearing cells and selection against plasmid-free cells. This region is divergently oriented to the 5' flanking region; and (3) a linker region which connects the 5' flanking region and the 3' flanking region. The 5' flanking region contains a functional origin of replication sequence. The 3' flanking region includes a nucleic acid sequence encoding for antibiotic resistance. The linker region includes a multicloning site element for inserting a nucleic acid cassette, as well as a transcriptional terminator element to ensure transcription of the antibiotic resistance sequence does not transcribe through the nucleic acid cassette. The multicloning site, or polylinker, is a region of nucleic acids that allow the cloning of other nucleic acid sequences into the plasmid backbone. These include multiple clustered restriction enzyme cleavage sties.

The term "plasmid" as used herein refers to a construction comprised of genetic material designed to direct transformation of a targeted cell. The plasmid consist of a plasmid backbone. A "plasmid backbone" as used herein contains multiple genetic elements positional and sequentially oriented with other necessary genetic elements such that the nucleic acid in a nucleic acid cassette can be transcribed and when necessary translated in the transfected cells. The term plasmid as used herein can refer to nucleic acid, e.g., DNA derived from a plasmid vector, cosmid, phagemid or bacteriophage, into which one or more fragments of nucleic acid may be inserted or cloned which encode for particular genes. This includes the construction comprised of extrachromosomal genetic material, usually of a circular duplex of DNA which can replicate independently of chromosomal DNA.

As used herein, plasmids are gene therapy backbones, not expression vectors. Plasmid backbones are defined by elements whose primary function is manifested in bacteria, e.g., E. coli, as well as other cells. This does not limit the scope of plasmids or plasmid backbones purely to bacteria in any way, as one skilled in the art will recognize that such elements can have phenotypic effects in both bacterial organisms as well as eukaryotes. A plasmid backbone is different from the plasmid in that the plasmid contains the nucleic acid cassette and the plasmid backbone. A nucleic acid cassette (see below) contains the therapeutic gene and associated regulatory elements which has an intended site of action—cells of human patients or animals.

The plasmid backbone can contain one or more unique restriction sites within the backbone. The plasmid may be capable of autonomous replication in a defined host or organism such that the cloned sequence is reproduced. The plasmid can confer some well-defined phenotype on the host organism which is either selectable or readily detected. The plasmid or plasmid backbone may have a linear or circular configuration. The components of a plasmid can contain, but is not limited to, a DNA molecule incorporating: (1) DNA; (2) the plasmid backbone; (3) a sequence encoding a therapeutic or desired product; and (4) regulatory elements for transcription, translation, RNA stability and replication.

The purpose of the plasmid is to generally be used in human gene therapy for the efficient delivery of nucleic acid sequences to and expression of therapeutic genes in a cell or tissue. In particular, the purpose of the plasmid is to achieve high copy number, avoid potential causes of plasmid instability and provide a means for plasmid selection. As for expression, the nucleic acid cassette contains the necessary elements for expression of the nucleic acid within the cassette. Expression includes the efficient transcription of an inserted gene, nucleic acid sequence, or nucleic acid cassette with the plasmid. Expression products may be proteins, polypeptides or RNA. The nucleic acid sequence can be contained in a nucleic acid cassette. Expression of the nucleic acid can be continuous or regulated.

The term "plasmid" as used herein does not include viral vectors. A "viral vector" in this sense is one that is physically incorporated in a viral particle by the inclusion of a portion of a viral genome within the vector, e.g., a packaging signal, and is not merely DNA or a located gene taken from a portion of a viral nucleic acid. Thus, while a portion of a viral genome can be present in a plasmid of the present invention, that portion does not cause incorporation of the plasmid into a viral particle and thus is unable to produce an infective viral particle.

A plasmid as used herein can also include within its backbone elements which enable extra-chromosomal (episomal) replication of DNA in eukaryotic cells. Plasmids capable of episomal replication are maintained as extra-chromosomal material and can replicate. These sequences are not eliminated by simple degradation but continue to be copied. These sequences may be derived from various genomes. These provide prolonged or "persistent" expression as described below.

The term "persistent expression" as used herein refers to introduction of genes into the cell together with genetic elements which enable episomal (i.e., extrachromosomal) replication and/or maintenance of the genetic material in the cell. This can lead to apparently stable transformation of the cell without the integration of the novel genetic material into the chromosome of the host cell.

"Stable expression" as used herein relates to the introduction of genetic material into chromosomes of the targeted cell where it integrates and becomes a permanent component of the genetic material in that cell. Gene expression after stable introduction can permanently alter the characteristics of the cell and its progeny arising by replication leading to stable transformation.

The term "nucleic acid sequence," "gene," "nucleic acid," "sequence" or "nucleic acid cassette" as used herein refers to the genetic material of interest which can express a protein, peptide, or RNA after it is incorporated transiently, permanently or episomally into a cell. The nucleic acid can be positionally and sequentially oriented in a plasmid with other necessary elements such that the nucleic acid can be transcribed and, when necessary, translated in the cells.

A variety of proteins and polypeptides can be encoded by the sequence in a nucleic acid cassette, i.e., "therapeutic gene," in the transformed/transfected tissue or cell. Those proteins or polypeptides which can be expressed include hormones, growth factors, regulatory factors, structural proteins, nuclear proteins, cytoplasmic proteins, mitochondrial proteins, secreted proteins, plasmalemma-associated proteins, serum proteins, lipoproteins, glycoproteins, phosphoproteins, enzymes, clotting factors, apolipoproteins, receptors, drugs, oncogenes, tumor antigens, tumor suppressors, viral antigens, parasitic antigens, protozoal antigens and bacterial antigens. In addition, the nucleic acid cassette can code for antisense RNA or ribozymes as well. These are only examples and are not meant to be limiting in any way. The compounds which can be incorporated are only limited by the availability of the nucleic acid sequence for the protein or polypeptide to be incorporated. One skilled in the art will readily recognize that as more proteins and polypeptides become identified they can be integrated into the plasmid system of the present invention and expressed in animal or human tissue.

The term "genetic material" as used herein refers to contiguous fragments of DNA or RNA. The genetic material which is introduced into targeted cells can be any DNA or RNA. For example, the nucleic acid can be: (1) normally found in the targeted cells, (2) normally found in targeted cells but not expressed at physiologically appropriate levels in targeted cells, (3) normally found in targeted cells but not expressed at optimal levels in certain pathological conditions, (4) not normally found in the targeted cells, (5) novel fragments of genes normally expressed or not expressed in targeted cells, (6) synthetic modifications of genes expressed or not expressed within targeted cells, (7) any other DNA which may be modified for expression in targeted cells and (8) any combination of the above.

The term "gene expression" or "nucleic acid expression" as used herein refers to synthesis of the gene product of the gene's genetic material from the transcription and translation process. Expression includes the polypeptide chain translated from an mRNA molecule which in turn is transcribed from a gene. If the RNA transcript is not translated, e.g., rRNA, tRNA, the RNA molecule represents the gene product. In the present invention such expression refers to expression of the nucleic acid cassette.

The term "cells" or "cell" as used herein refers to a membrane-enveloped protoplasmic body capable of independent reproduction. Cells can be maintained, or propagated, in vivo, in vitro or in tissue culture and capable of being transformed by plasmids as discussed herein. As used herein "tissue" refers to a population consisting of cells of the same kind performing the same function.

The term "flanking region" as used herein refers to nucleotide sequences on either side of an associated gene or nucleic acid sequence. Flanking regions can be either 5' or 3' to a particular gene or sequence in question. In general, flanking sequences contain necessary elements for replication, selection and maintenance of a plasmid, or expression of an inserted nucleic acid cassette or gene. Such elements include, but are not limited to, sequences such as replication origin, transcriptional terminator sequences, operator sequences, antibiotic resistant genes, multicloning sites or restriction sites. These are meant to be examples only and nonlimiting.

The term "regulates," or "regulation" as used herein refers to sequences involved in control of a response or action. This includes sequences involved in regulating, controlling or affecting the expression of structural genes, or the replication, selection or maintenance of a plasmid. Examples include attenuators, operators and promoters. These are only examples and are meant to be nonlimiting.

The term "attenuators" as used herein refers to a nucleotide sequence that is located upstream of operons which encode the enzymes that are involved in the synthesis of amino acids. The expression of such operons is switched on and off by controlling the transcription of the messages for these operons. The term "operon" is defined below. The term "promoter" as used herein refers to a region on a DNA molecule to which an RNA polymerase binds and initiates transcription. In an operon, the promoter is usually located at the operator end, adjacent but external to the operator. The nucleotide sequence of the promoter determines both the nature of the enzyme that attaches to it and the rate of RNA synthesis. The term "copy number" as used herein refers to the number of plasmids in a cell that result from replication of a plasmid in a host. The copy number of plasmids per host cell can range from 1 to more than 1000.

The term "replication origin" as used herein refers to a nucleotide sequence at which DNA synthesis for the purpose of replicating the nucleic acid sequence begins. This is generally termed an ori site. Circular bacterial generally have a single ori site, whereas there are many ori sites on each eukaryotic chromosome. This term includes replicons, which as used herein refers to a genetic element that behaves as an autonomous unit during DNA replication. In bacteria, the chromosome functions as a single replicon, whereas eukaryotic chromosomes contain hundreds of replicons in series.

The term "plasmid-containing cell" or "plasmid-bearing" as used herein refers to a cell transfected or transformed with a plasmid. Transfected and transformed are defined in more detail below.

As used herein, the term "divergently oriented" refers to divergent transcription. This includes the transcriptional orientation of different DNA segments such that transcription progresses in opposite directions from a central region. In particular, this refers to the 5' flanking region and the 3' flanking region of the present invention. Divergent orientation helps avoid transcription from the antibiotic resistant gene from transversing the origin of replication. Read through transcription from neighboring elements into the plasmid origin can lead to plasmid instability.

The term "antibiotic resistance" as used herein refers to the acquisition of tolerance to a specific antibiotic by a microorganism that was previously adversely affected by the drug. Such resistance generally results from a mutation or the acquisition of resistance due to plasmids containing the resistance gene transforming the micro-organism.

The term "linker region" as used herein refers to DNA which connects flanking regions of plasmid. The linker region includes multicloning sites which contain recognition sites for specific restriction endonucleases and transcriptional terminator-sequence. Linker regions may be ligated to the ends of DNA fragments prepared by cleavage with some other enzyme. A linker region can also have unique restriction endonuclease sites at the location of the start and stop codon to ligate the 5' flanking region, as well as the 3' flanking region to the nucleic acid of the linker. In particular, the linker region provides recognition sites, i.e., the "multicloning sites," for inserting the nucleic acid cassette which contains a specific nucleic sequence to be expressed. These recognition sites may be an endonuclease site in the linker, such as BamHI, EcoRI, HindIII, ClaI, NotI, XmaI, BglII, PacI, XhoI, NheI, SfiI. These are only examples and not meant to be limiting. The multicloning site permits easy insertion of expression elements such as promoters, therapeutic genes, etc. For example, the multicloning site in pBluescript KS+ provides 17–23 unique restriction sites useful in inserting expression elements or previously constructed nucleic acid cassettes.

The term "transcriptional terminator element" as used herein refers to nucleotide sequences that function to stop transcription. In the present invention this sequence is located within the linker region 3' to the multicloning sequence but can be located at other sites in the plasmid. In one embodiment, the terminators are derived from $E.$ $coli$ rrnB operon. These sequences ensure transcription of the nucleic acid sequence does not read through into other functional regions of the plasmid. The term "transcription" or "transcribe" as used herein refers to the process by which RNA molecules are formed upon DNA templates by complementary base pairing. This process is mediated by RNA polymerase.

In addition to the first aspect, the plasmid may also include nucleic acid restriction sites which flank the elements of the plasmid, such as the replication origin, the antibiotic resistant nucleic acid, the linker region, and the terminator sequence. Furthermore, the plasmid may also contain additional functional elements which can be inserted into the above restriction sites. Such functional elements include partitioning loci or multimer resolution loci. The plasmid allows such functional and transcriptional regulatory elements to be easily and directionally cloned into the plasmid backbone. Furthermore, the backbone also has additional nucleic acid sequences which insulate the functional elements of the complete plasmid from the effect of other elements.

As used herein the terms "nucleic acid restriction sites" or "restriction sites" refer to deoxyribonucleic acid sequences at which a specific restriction endonucleases cleave the molecule.

The term "functional element" as used herein refers to any nucleic acid sequence that confers a detectable phenotype on a plasmid or on a cell containing that plasmid. Examples of functional elements include partitioning loci, multimer resolution loci, replication origins.

As used herein the term "partitioning loci" refers to nucleic acid sequences that ensure or help ensure that at least one copy of a plasmid is transmitted to each new cell during cell division. An example of a partitioning locus is the parA parb parc complex of plasmid P1.

The term "multimer resolution loci" as used herein refers to nucleic acid sequences that ensure or help ensure that a plasmid is maintained in a monomeric form. In a preferred embodiment, the plasmid described above may have a replication origin from the plasmid pMM1, the antibiotic resistance nucleic acid containing the neo gene, the multicloning site derived from the polylinker sequence from pBluescript KS+, and the transcriptional terminator sequence derived from rrnBT$_1$T$_2$ from the plasmid pKK223-3. As one skilled in the art will recognize, these elements can be further defined by routine methodology, to determine their equivalent elements.

In a second related aspect, the present invention features a method of using the plasmid discussed above. This method comprises the steps of contacting a cell with a plasmid for sufficient time to transform the cell. The plasmids of this aspect also include a nucleic acid cassette. The term "contacting" as used herein refers to transfecting or transfection as defined below.

The term "transform" or "transformation" as used herein refers to transient, stable or permanent changes in the characteristics (expressed phenotype) of a cell by the mechanism of gene transfer. Genetic material is introduced into a cell in a form where it expresses a specific gene product or alters the expression or effect of endogenous gene products.

The term "stable" as used herein refers to the introduction of gene(s) into the chromosome of the targeted cell where it integrates and becomes a permanent component of the genetic material in that cell. Gene expression after stable transformation/transfection can permanently alter the characteristics of the cell leading to stable transformation. An episomal transformation is a variant of stable transformation in which the introduced gene is not incorporated in the host cell chromosomes but rather is replicated as an extrachromosomal element. This can lead to stable transformation of the characteristics of a cell. "Transiently" as used herein refers to the introduction of a gene into a cell to express the nucleic acid, e.g., the cell expresses specific proteins, peptides or RNA, etc. The introduced gene is not integrated into the host cell genome and is accordingly eliminated from the cell over a period of time. Transient expression relates to the expression of a gene product during a period of transient transfection.

Transformation can be performed by in vivo techniques as described below or ex vivo techniques in which cells are co-transfected with a plasmid containing a selectable marker. This selectable marker is used to select those cells which have become transformed. This includes antibiotic resistant systems as discussed below. It is well known to those skilled in the art the type of selectable markers to be used with transformation studies. Transformation can be tissue specific to regulate expression to the nucleic acid predominantly in the tissue of choice.

Transformation of the cell may be associated with production of a variety of gene products including protein and RNA. These products may function as intracellular or extracellular structural elements, ligands, hormones, neurotransmitters, growth regulating factors, enzymes, serum proteins, receptors, carriers for small molecular weight compounds, drugs, immunomodulators, oncogenes, tumor suppressors, toxins, tumor antigens, antigens, antisense inhibitors, triple strand forming inhibitors, ribozymes, or as a ligand recognizing specific structural determinants on cellular structures for the purpose of modifying their activity. Other examples can be found above in the discussion of nucleic acid cassette. The product expressed by the transformed cell depends on the nucleic acid of the nucleic acid cassette. This list is only an example and is not meant to be limiting. In the present invention the nucleic acid to be expressed depends on what gene or sequence has been incorporated into the cassette.

Transformation can occur via various mechanisms such as transfection, electroporation or particle bombardment. As used herein the term "transfected" or "transfection" refers to the incorporation of foreign DNA into cultured cells by exposing them to such DNA. This would include the introduction of DNA by various delivery methods, e.g., via vectors or plasmids.

Methods of transfection will include microinjection, $CaPO_4$ precipitation, liposome fusion (e.g., lipofection) or use of a gene gun. The term "transfection" as used herein refers to the process of introducing DNA into a cell. Following entry into the cell, the transfected DNA may: (1) recombine with that of the host; (2) replicate independently as a plasmid or temperate phage; or (3) be maintained as an episome without replication prior to elimination. Cells may be naturally able to uptake DNA.

Particular cells which are not naturally able to uptake DNA require various treatments, as described above, in order to induce the transfer of DNA across the cell membrane. This also includes incorporation.

"Incorporate" or "incorporation" refers to uptake or transfer of the plasmid into a cell such that the plasmid is capable of delivering the nucleic acid of the therapeutic gene product to be expressed within the cell.

Significantly, incorporation may involve, but does not require, integration of the DNA expression vector or episomal replication of the plasmid. Incorporation in this sense includes the short term persistence of the DNA expression vector in the cell before it is eliminated by degradation or translocation to other compartments.

Incorporation includes expression of the nucleic acid cassette by cells, whether it is transient expression, persistent expression or stable expression. "Transient expression" as used herein relates to the introduction of genetic material into a cell to express specific proteins, peptides or RNA, etc. The introduced genetic material is not integrated into the host cell genome, or replicated and is accordingly eliminated from the cell over a period of time by degradation or translocation to other compartments. These terms are defined in more detail above.

In a third aspect, the present invention features a plasmid as described above which also includes an operator sequence capable of binding specific transcription repressor proteins and derepressing a chromosomal operon. The operator sequences can be located 5' to the 5' flanking region and 5' to the 3' flanking region which is in divergent origin as discussed above. In addition, the operator sequence can also be located 3' to said 5' flanking region and 5' to the linker region. The plasmid can also be present in more than one copy, with each copy the same or different operator sequences. The location of such can be as described above.

As used herein the term "operator sequence" refers to a specific nucleic acid sequence capable of interacting with a specific repressor, thereby controlling the function of genes in adjacent cistrons and regulator genes.

In general, a regulator gene is a gene whose primary function is to control the rate of synthesis of the products of other distant genes. The regulator gene controls the synthesis of a protein repressor, which inhibits the action of an operator gene and thus turns off the operon it controls. The repressor is present in small amounts. It may possess two sites, one of which can attach to the operator and one of which can bind an effector molecule. Once bound to an effector molecule, however, the repressor changes shape and cannot attach to the operator. An operon is a unit of nucleic acid sequence consisting of one or more cistrons that function coordinately under the control of an operator sequence.

Thus, the repressor is a protein, synthesized by a regulator gene, that binds to an operator locus and blocks transcription of that operon. The repressor causes repression of transcription, i.e., the inhibition of transcription or translation when a repressor protein binds to an operator locus on DNA or to a specific site on a mRNA.

The term "derepressing" as used herein refers to an increased synthesis of gene product accomplished by preventing the interaction of a repressor with the operator sequence of the operon in question. In the case of inducible enzyme systems, the inducer derepresses the operon. A mutation of the regulatory gene that blocks synthesis of the repressor or a mutation of the operator gene that renders it insensitive to a normal repressor will also result in derepression.

As used in the present invention, antibiotic resistance genes are incorporated either into the plasmid backbone as discussed above or under a different aspect of the invention, into the *E. coli* chromosome under the control of heterologous promoter/repressor systems. In the absence of a plasmid, the chromosomally encoded repressor prevents transcription of the integrated resistance gene, and the host is sensitive to antibiotic. To induce expression of the resistance gene, a plasmid is introduced that contains operator sequences recognized by the repressor protein. If the plasmid is present in high copy number, the repressor protein will bind to sites on the plasmid molecules. This leaves less repressor to block transcription of the resistance gene, which renders the cells resistant to antibiotic. This phenomenon, where an operator sequence present on a high copy number plasmid derepresses a chromosomal operon, is called "repressor titration."

Thus, initial plasmids described in the patent have antibiotic resistance genes in the plasmid backbone. Other aspects of the invention deal with removal of the antibiotic resistance gene from the plasmid and incorporation into the bacterial genome to be controlled by repressor titration with operator sequences in the plasmid backbone. This leads to the generation of new versions of selectable plasmids which do not contain antibiotic genes themselves.

A fourth related aspect of the present invention features methods for transformation of a cell with the plasmids of the present invention. These methods comprise the steps of contacting a cell with a plasmid of the present invention for sufficient time to transform the cell. The plasmids contain a nucleic acid cassette, as defined above, for delivery of a gene product to the cell. As discussed above, the transformations can be in vivo or ex vivo.

A fifth related aspect of the present invention features a plasmid for delivery of a nucleic acid sequence to cells which includes a 5' flanking region, a 3' linker region and an operator sequence. The 5' flanking region regulates the plasmid copy number and includes a replication origin sequence. The 3' linker region is 3' to the 5' flanking region and includes a multicloning site element for inserting a nucleic acid cassette. The operator sequence is capable of derepressing a chromosomal operon. As discussed above, the operator sequence can be located in various places within the plasmid and can be present in more than one copy, with each copy the same or different operator sequences. The above plasmid can also include a 3' flanking region which is located 3' to the linker region. This region includes a transcriptional terminator element and nucleic acid restriction sites.

A sixth related aspect of the present invention features a method for plasmid selection. The method comprises the steps of selecting a plasmid from a plurality of plasmids with nucleic acid cassettes by contacting a cell with one of the various plasmids for sufficient time to transform the cell. The plasmids used include a nucleic acid cassette. A plasmid can then be selected from the appropriately transformed cells. The antibiotic resistant nucleic acid sequence is removed from the plasmid at the flanking nucleic acid restriction sites. The plasmid is then recircularized.

The selected plasmid is then used to contact a second cell for a sufficient time to transform the second cell. The second cell contains at least one antibiotic resistant gene incorporated into the cell's chromosome under the control of a chromosomal operon (as described above). The operon is derepressed by the operator sequence present on the selected plasmid. The transformed cells which are resistant to antibiotics are then selected and the plasmid purified for further use.

As used herein the term "selection," "selected," or "selecting" refers to growing or maintaining cells under appropriate conditions such that only those cells with the desired characteristics or phenotypes may grow. An example is the growth of a bacterium, such as E. coli, in the presence of an antibiotic, such as ampicillin, so that E. coli cells containing a plasmid carrying the ampicillin resistance gene (blg) can grow, while cells lacking the plasmid are killed.

As used herein the term "appropriately transformed" refers to cells transformed with the desired characteristics.

As used herein the term "removal" refers to excising nucleic acid sequences from the plasmid and religning or connecting the plasmid after the sequence is removed. The term "recircularized" as used herein refers to relegation of the linear plasmid.

As used herein the term "control of a chromosomal operon" refers to genes which expression of is controlled by operator sequences and operons as defined above.

The term "purified" in conjunction with plasmids refers to purification of nucleic acid sequences. One skilled in the art will readily recognize the meaning of purification as used in the art.

A seventh aspect of the present invention features a method of plasmid selection which includes the steps of contacting the cell with a plasmid of above for sufficient time to transform the cell. The cell contains at least one antibiotic resistant gene incorporated into the cell's chromosome under the control of a chromosomal operon. The operon as discussed above is capable of derepression by repressor titration due to the operator sequence on the plasmid. The transformed cells resistant to antibiotic are then selected. The plasmid can then be isolated from the selected cells.

In addition to the above, the methods of use also include methods of administration of the plasmid. The term "administration" as used herein refers to the route of introduction of a plasmid or carrier of DNA into the body. The plasmids of the above methods and the methods discussed below may be administered by various routes. Administration may be intravenous, intramuscular, topical, oral, or by gene gun or hypospray instrumentation. Administration can be directly to a target tissue or through systemic delivery.

Administration will include a variety of methods, such as direct gene transfer into tissue by liposomes, proteoliposomes, calcium phosphate-co-precipitated DNA, DNA coupled to macro-molecular complexes, DNA transporters, DNA coated to micro-projectiles, coated plasmids, direct micro-injection, as well as tissue grafting. Direct gene transfer of plasmids can be administered by microinjection, electroporation, liposomes, proteoliposomes, calcium-phosphate-co-precipitation, tissue grafting, DNA coupled to macromolecular complexes, DNA transporters, gene gun and micro-projectiles. See, e.g., WO 93/18759, hereby incorporated by reference herein. The preferred embodiment is by direct injection. Routes of administration include intramuscular, aerosol, oral, topical, systemic, ocular, intraperitoneal, and/or intrathecal.

The term "effective amount" as used herein refers to sufficient plasmid administered to humans, animals or into tissue culture to produce the adequate levels of polypeptide, protein or RNA. One skilled in the art recognizes that the adequate level of protein/polypeptide or RNA will depend on the use of the particular vector. These levels will be different depending on the type of administration and treatment or vaccination.

Other features and advantages of the invention will be apparent from the following detailed description of the invention in conjunction with the accompanying drawings and from the claims.

Figure 1:
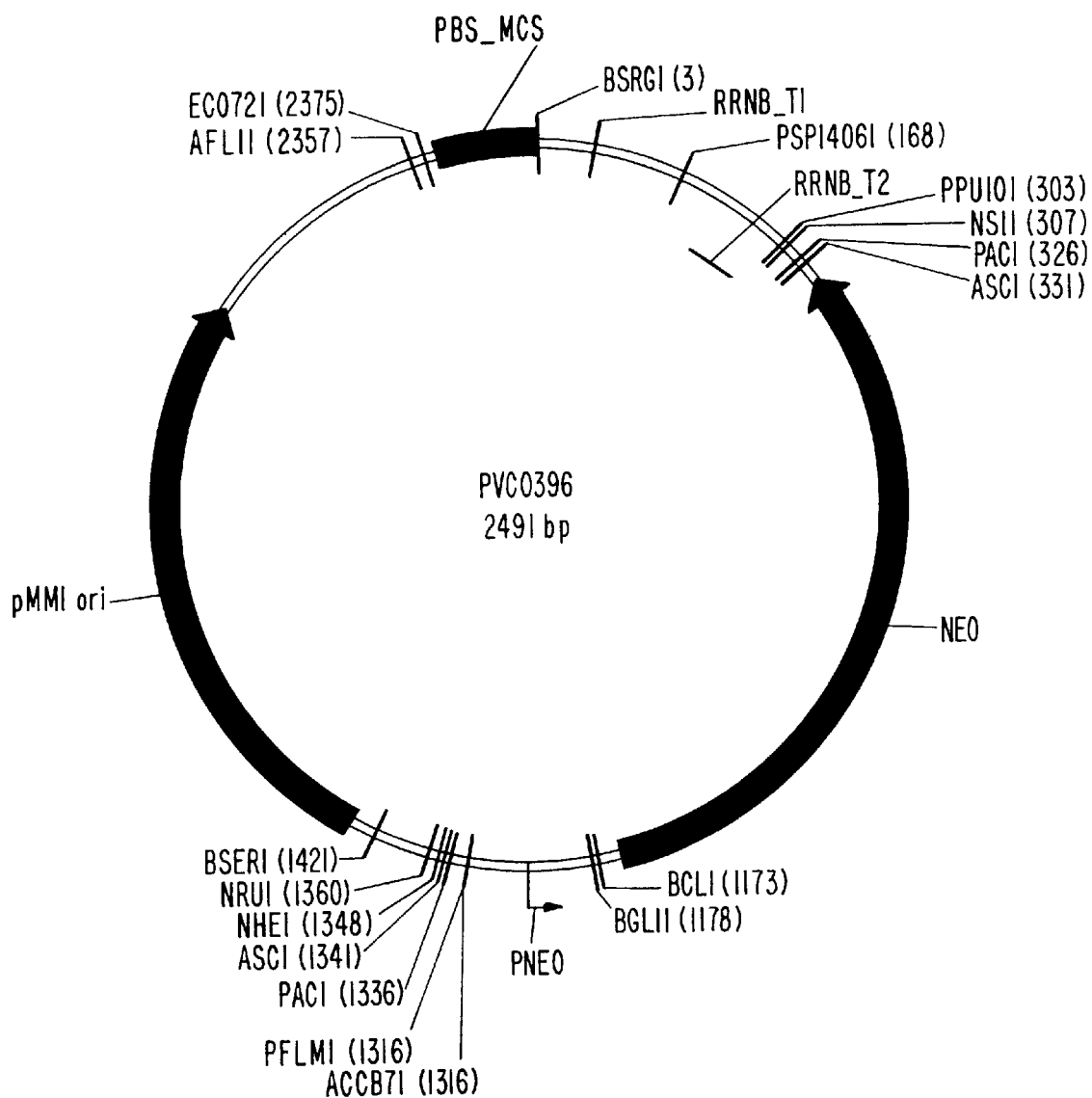
FIG. 1 is a schematic representation of PCV0396.

The drawings are not necessarily to scale, and certain features of the invention may be exaggerated in scale and shown in schematic form in the interest of clarity and conciseness.

DETAILED DESCRIPTION OF THE INVENTION

The following are examples of the present invention using various plasmid elements to design and construct plasmids for delivery of nucleic acid to various tissues. In particular, the following are specific examples of plasmid construct, pVC0396 and its derivatives. The utility of the plasmids of the present invention is noted by use in nonviral human gene therapy. These examples are offered by way of illustration and are not intended to limit the invention in any manner.

In the present invention, specific elements of plasmids can be used to provide functionalities to a plasmid for delivery of nucleic acid and thus provide functionalities within a transformed cell or animal containing such a plasmid. Various plasmid elements have a variety of effects that influence plasmid use as gene therapy vectors. This includes the relative position and orientation of plasmid elements. Those skilled in the art will recognize that specific portions of these regions or elements can be identified as containing the functional aspects providing the desirable property. Such elements can be readily defined using routine techniques or their equivalents. The success of such plasmids in nonviral human gene therapy requires careful optimization of all elements of the plasmid.

One of the key functionalities of the plasmid backbones affect the production/manufacture of plasmid DNA in bacteria, i.e., plasmid copy number in bacteria and the ability to select from plasmid-bearing bacterial cells during bacterial fermentation. In addition, how the plasmid elements that control such functions are organized on the plasmid influences how plasmids behave in eukaryotic cells and how efficiently the plasmids express a therapeutic protein or RNA.

Accordingly, this invention sets forth the design and construction of a series of novel plasmid backbones using various nucleic acid sequence elements. These backbones have been designed with a number of goals in mind, such as achieving regulated high copy number and avoiding potential causes of plasmid instability in bacteria, and providing means for plasmid selection that are compatible with human therapeutic use. Particular attention has been paid to the dual requirements of gene therapy plasmids. First, they must be suitable for maintenance and fermentation in *E. coli*, so that large amounts of DNA can be produced and purified. Second, they must be safe and suitable for use in human patients and animals. The first requirement calls for high copy number plasmids that can be selected for and stably maintained relatively easily during bacterial fermentation. The second requirement calls for careful attention to elements such as selectable markers and other coding sequences that present potential safety concerns in humans and animals.

In particular, the following examples set forth elements of pVC0396. This plasmid is composed of: (1) a high copy number replication origin, (2) the neo gene for antibiotic selection with kanamycin, (3) transcription termination sequences, and (4) a multicloning site for incorporation of various nucleic acid cassettes. Importantly, this vector is designed to be modular or flexible, i.e., it has the ability to easily add, remove and modify plasmid elements to maximize the empirical utility of the vector. Such flexibility is achieved by using one or more unique restriction sites flanking each element to permit easy removal, replacement, or modification as needed. These unique sites also permit easy incorporation of additional plasmid elements, such as partition or multimer resolution loci, if desired.

Furthermore, all elements of these backbones are modular and may be easily removed or replaced as needed. Thus, other elements such as replication origins, selectable markers, and polylinkers can easily be used to replace the ones present in these backbones. Furthermore, additional elements such as partitioning loci or multimer resolution sites can easily be added to the existing backbones to address problems that may potentially arise in some constructs.

In addition, the examples below describe the development of operator selection, a system in which short operator sequences on high copy number plasmids can be used as selectable markers for plasmid maintenance. This system is very flexible and solves a number of potential problems associated with the use of intact antibiotic resistance genes on gene therapy plasmids.

The use of operator selection, i.e. repressor titration, in these backbones is particularly advantageous for the field of human gene therapy. This technique permits the use of antibiotics to select for plasmid maintenance in bacteria during the manufacture of plasmid DNA for therapeutic purposes, based on the presence of a ~20-bp selectable element in the plasmid itself. This eliminates a number of potential concerns about antibiotic resistance genes cloned on the plasmid, but retains the advantages offered by antibiotics, namely low cost, efficient inhibition or killing of plasmid free cells, and ease of use. Operator selection eliminates concerns that the antibiotic resistance gene may be a potential safety hazard when transferred to human patients, either directly or by increasing the possibility of generating antibiotic resistant pathogens. Operator selection also eliminates the potential metabolic energy cost to the host bacterium associated with expression of an antibiotic resistance gene present on a high copy number plasmid.

One skilled in the art will recognize that variations on the approaches described herein are possible. Operator selection is adaptable to virtually any combination of a repressible promoter and an antibiotic resistance gene or other selectable element. The wide range of repressor operator systems previously shown to be subject to repressor titration indicates that many independent and compatible systems can be constructed. An attractive feature of the approach is that repressor/promoter/operator systems can be used that have no effect on any of the *E. coli* host genes. The tetO system described herein is one example. There are no naturally occurring genes in *E. coli* that are regulated by tetr . Thus, depressing the tet promoter, $P_{tetA}$, does not affect gene expression of the host and cell metabolism is not altered, apart from obvious effects that expression of chromosomally integrated resistance gene is expected to have. Other such systems that might be employed include phage or plasmid repressor/operator systems, or repressor/operator systems from non-*E. coli* sources that have no counterpart in *E. coli*.

The lambda integration system allows easy conversion of any desired *E. coli* strain to one appropriate for operator selection. The only requirement is that the strain must be lambda⁻ and contain the attB site. The plasmids described herein, as well as various derivatives of them, have substantial utility in the nonviral gene therapy field.

Bacterial Strains and Plasmids

The following is a list of bacterial strains and plasmids used.

| Bacterial strains strain | genotype |
|---|---|
| *E. coli* DH5α | F⁻ φ80dlacZΔM15 Δ(lacZYA-argF)U169 endA1 recA1 hsdR17($r_k^-$ $m_k^+$) deoR thi-1 supE44 λ⁻ gyrA96 relA1 |
| *E. coli* GMS001 | F⁻ φ80dlacZΔM15 Δ(laCZYA-argF)U169 endA1 recA1 hsdR17($r_k^-$ $m_k^+$) deoR thi-1 supE44 λ⁻ gyrA96 relA1 [tetR⁺ tetA::cat (integrated at attB)] |
| *E. coli* GMS002 | F⁻ φ80dlacZΔM15 Δ(lacZYA-argF)U169 endA1 recA1 hsdR17($r_k^-$ $m_k^+$) deoR thi-1 supE44 λ⁻ gyrA96 relA1 [lacI⁺ lacZ::neo (integrated at attB)] |

-continued

| | |
|---|---|
| E. coli GMS003 | F⁻ φ80dlacZΔM15 Δ(lacZYA-argF)U169 endA1 recA1 hsdR17(r$_k^-$ m$_k^+$) deoR thi-1 supE44 λ⁻ gyrA96 relA1 [tetR⁺ tet-A::cat lacI⁺ lacZ::neo (integrated at attB)] |
| Plasmids | |
| plasmid name | relevant features |
| pBluescript KS+ | general cloning vector, Amp$^r$ |
| pCT0132 | pBluescript II KS– containing CAT (chloramphenicol acetyltransferase) gene |
| PGM501 | pLDR11 containing Tn10 tetR +P$_{tetA}$ |
| PGM502 | pGM501 containing the CAT gene downstream of P$_{tetA}$ |
| pGM503 | pLDR11 containing Tn5 neo |
| pGM504 | pGM503 containing lacIPO upstream of neo |
| pGM505 | pGM502 containing the lacIPO::neo fragment from pGM504 |
| pGM506 | pGM510 containing tetO |
| pGM507 | pGM510 containing lacO |
| pGM508 | pGM510 containing tetO and lacO |
| pGM509 | pVC0396 cdntaining tetO and lacO |
| pGM510 | Tet$^r$ derivative of pUC18 in which the bla gene and the lac operator have been deleted |
| pKK223-3 | plasmid containing the strong E. coli transcription terminators rrnBT$_1$T$_2$ |
| pLDR8 | pSC101-ori$^{ts}$, λ P$_R$::int, λ cI857, Tet$^r$ |
| pLDR11 | Tet$^r$, Amp$^r$, lambda attP |
| pMM1 | ColE1 derivative containing temperature inducible replication origin, Amp$^r$ |
| pNEO | Tn5 neo |
| pNK81 | pBR322 hisG::Tn10 |
| pSL1180 | pUC-based plasmid containing a super-polylinker |
| pSPORT1 | lacIPO |
| pVC0289 | derivative of pBluescript KS+, neo (Kan$^r$) |

For routine growth of bacteria, L-broth, "LB" medium was used. Antibiotics were purchased in the industry. The following concentrations were used throughout the experiments: ampicillin, 50 μg/mL; kanamycin, 50 μg/mL; chloramphenicol, 30 μg/mL; tetracycline, 15 μg/mL; anhydrotetracycline 0.1 μg/mL. Cloned nucleic acid fragments were integrated into the attB site of the E. coli chromosome according to the procedure of Diederich, et al., *Plasmid* 28:14–24 (1992).

Nucleic Acid Manipulations

Restriction enzymes, oligonucleotides, as well as other necessary enzymes for nucleic acid manipulations were purchased from the industry and used according to the manufacturer's instructions. Transformation, nucleic acid preparation, gel electrophoresis, and southern blotting were performed according to published procedures (Sambrook, et al., *Molecular Cloning: A Laboratory Manual*, 2nd edition, 1989, Cold Spring Harbor Laboratory Press, Cold Spring Harbor, N.Y.).

Construction and Characterization of PVC0396

The physical and genetic map for pVC0396 is shown in FIG. 1. Relevant features are: pMM1 ori, the temperature inducible replication origin from plasmid pMM1; NEO, the neomycin/kanamycin resistance gene from Tn5; P$_{neo}$, the neo gene promoter; RRNB_T1 and RRNB_T2, the tandem transcriptional terminators from the E. coli rrnB operon; PBS_MCS, the polylinker (or multicloning site) from pBluescript KS+. Also shown are unique restriction enzyme recognition sites that flank each of the major elements of pVC0396. These sites can be used to insert additional elements or to substitute or rearrange the existing elements of pVC0396.

Figure 2A:
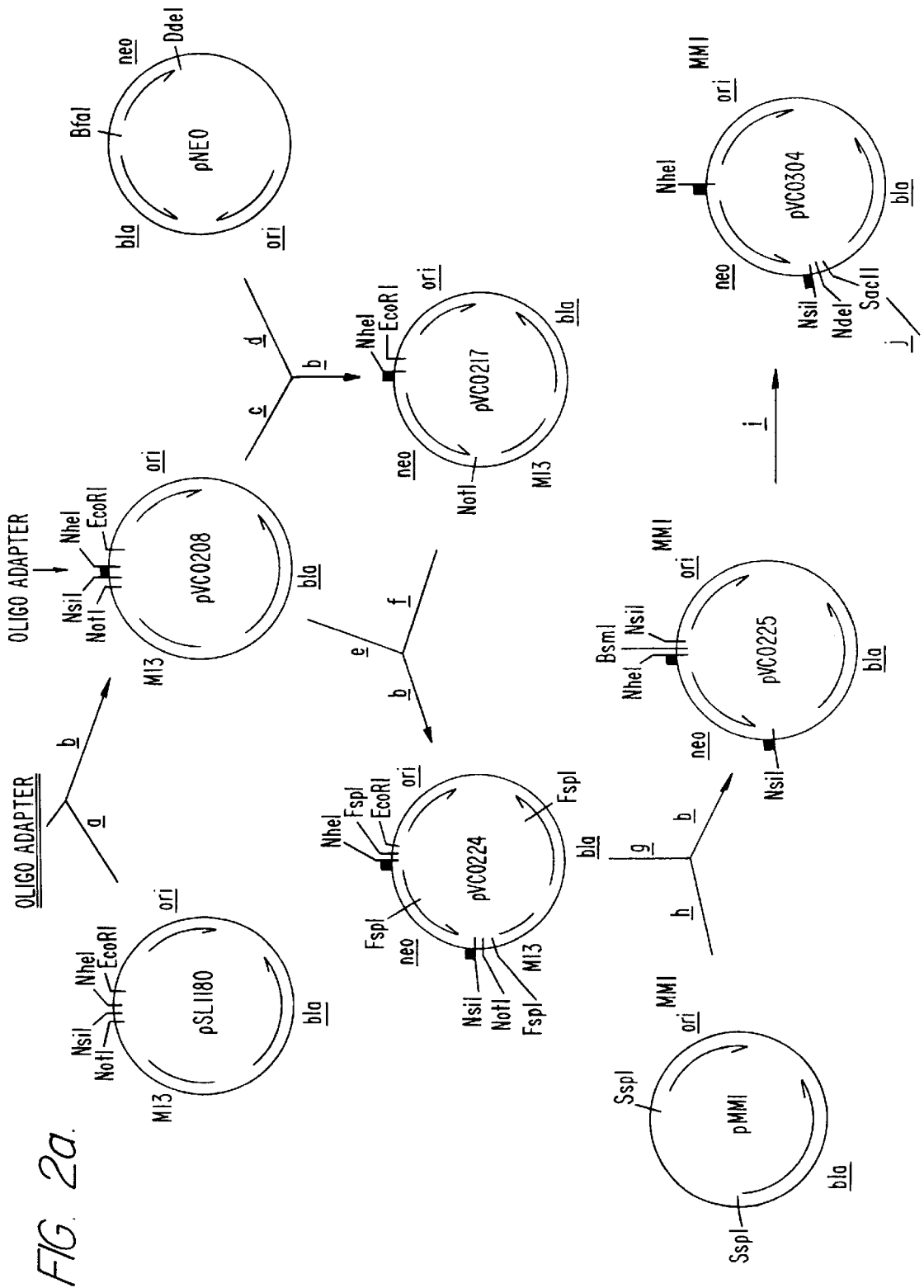
FIG. 2 is a schematic representation of the construction of PCV0396.
Figure 2B:
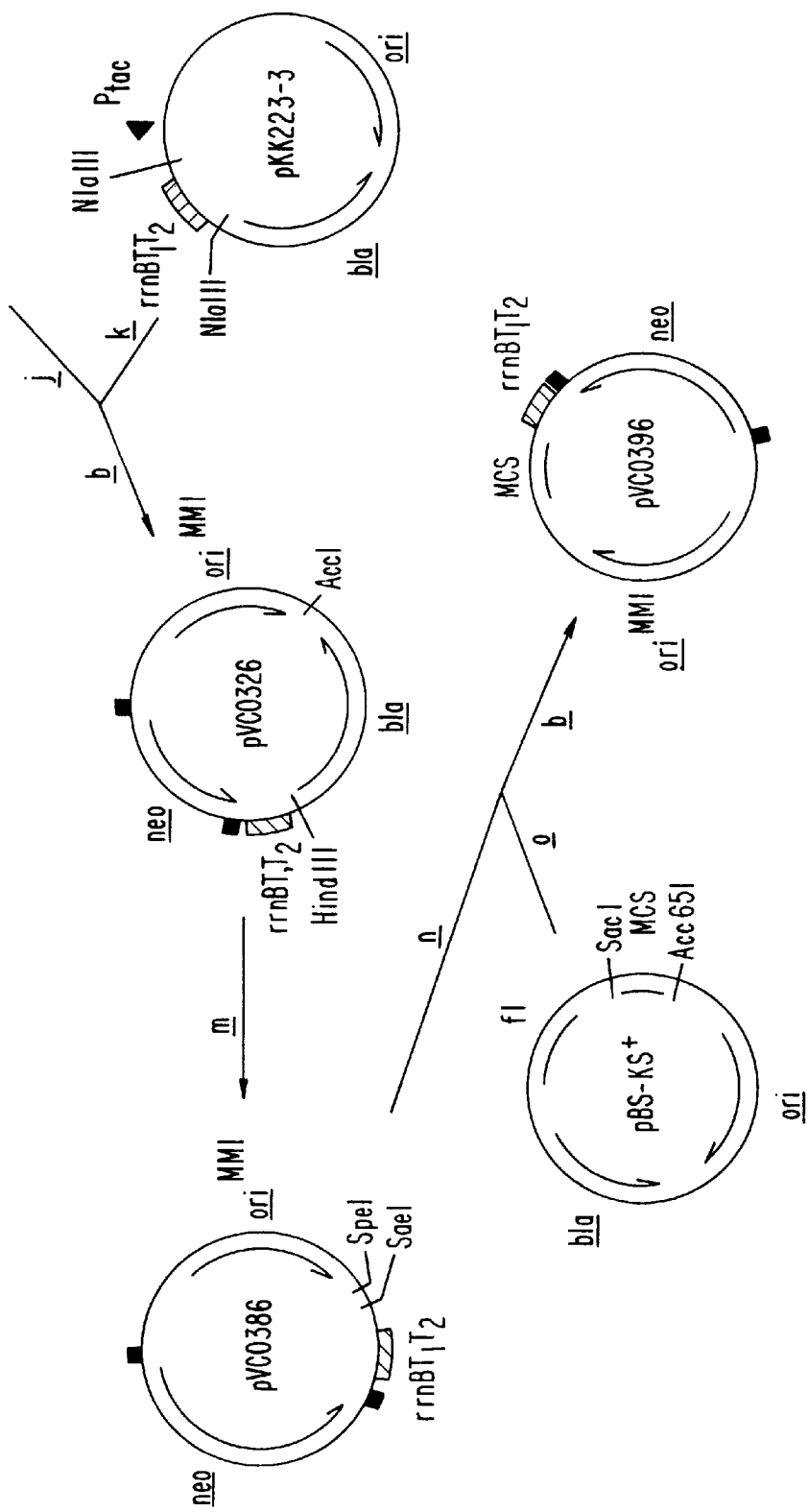

FIG. 2 describes the construction of pVC0396. The oligo adapter consisted of two synthetic oligos with the following sequence: 5'-TGG-CCA-GTG-TGG-CCT-TAA-TTA-AGG CGC-GCC-G-3' (SEQ ID NO. 1) and 5'-CTA-GCG-GCG-CGC-CTT-AAT-TAA-GGC-CAC-ACT-GGC-CAT-GCA-3' (SEQ ID NO. 2). These oligos are complementary, and when annealed, result in one NsiI end and one NheI end. Relevant reactions at each step of the construction are as follows: PSL1180 was digested with NsiI and NheI restriction enzymes. The large fragment was gel purified. The indicated DNAs were ligated and then transformed in *E. coli* DH5α. PVC0208 was digested with NsiI and treated with T4 DNA polymerase plus 4×dNTPs. pNEO was digested with BfaI and DdeI and treated with T4 DNA polymerase plus 4×dNTPs. The 965-bp neo fragment was gel-purified. PVC0208 was digested with NheI. It was then treated with T4 DNA polymerase plus 4×dNTPs, and digested with EcoRI. The large 3258-bp fragment was gel-purified.

PVC0217 was digested with NotI and treated with T4 DNA polymerase plus 4×dNTPs. It was then digested with EcoRI. The 1133-bp fragment containing neo was gel-purified. pVC0224 was partially digested with FspI. The 1303-bp fragment containing neo was gel purified. PMM1 was digested with SspI. The 2611-bp fragment containing bla and ori were gel purified.

PVC0255 was digested with BsmI and treated with T4 DNA polymerase plus 4×dNTPs. Fragments were religated and transformed into *E. coli* DH5α. PVC0304 was digested with NdeI plus SacII and treated with T4 DNA polymerase plus 4×dNTPs. The 3863-bp large fragment was gel-purified. PKK223-3 was digested with NlaIII and treated with T4 DNA polymerase plus 4×dNTPs. The 288-bp fragment containing rrnBT$_1$T$_2$ was gel-purified. PVC0326 was digested with HindIII and AccI then treated with T4 DNA polymerase plus 4×dNTPs. The 2398-bp large fragment (lacking bla) was gel- purified and then ligated, and transformed into *E. coli* DH5α.

PVC0386 was digested with SpeI and treated with T4 DNA polymerase plus 4×dNTPs. It was then digested with SacI. The 2385-bp large fragment was then gel-purified. pBluescript KS+was digested with Acc65I then treated with T4 DNA polymerase plus 4×dNTPs and then digested with SacI. The 106-bp fragment containing the polylinker was gel-purified.

All intermediate plasmids described in FIG. 2 were tested to confirm the correct size, insert orientation and restriction pattern at each step. Gene symbols are: ori, plasmid replication origin; ori$^{MM1}$, plasmid replication origin derived from pMM1; M13, sequences derived from bacteriophage M13; bla, β-lactamase (Amp$^r$) gene; neo, neomycin/kanamycin resistance gene from Tn5; rrnBT$_1$T$_2$, tandem transcriptional terminators from the E. coli rrnB operon; f1, sequence from bacteriophage f1; MCS, polylinker (multicloning site) sequence.

The plasmid pVC0396 consists of 2491 base pairs and contains the following elements: (1) the plasmid replication origin of plasmid pMM1; (2) the neo gene from transposon Tn5, derived from the plasmid pNEO and encoding resistance to kanamycin, neomycin, and G418; (3) a series of 8-bp restriction sites flanking the neo gene to permit easy removal if desired; (4) the rrnBT$_1$T$_2$ terminator element derived from pKK223-3 (20); and (4) the multicloning site element from pBluescript KS+. PVC0396 was designed with the overall goals of minimizing plasmid size, avoiding potential negative interactions between elements, permitting easy subcloning of expression cassettes from other vectors, allowing stringent selection for plasmid maintenance, and minimizing potential safety concerns for human therapeutic use. Furthermore, pVC0396 is designed to be modular, allowing easy manipulation of existing elements and easy addition of extra elements, as desired.

The replication origin for pVC0396 is derived from plasmid pMM1, a temperature sensitive copy-up mutant derived from ColE1. pMM1 has a low copy number when maintained at 30° C., but it is amplified to high copy number when maintained at or above 37° C. The copy number of pMM1 in cells grown to stationary phase at 37° C. or 42° C. is about 2- to 5-fold higher than for the pUC-based plasmid pBluescript II KS−. This high copy number is desirable because it permits isolation of greater quantities of plasmid DNA from a given volume of bacterial culture. To confirm that the higher copy number of pMM1 is maintained in pVC0396, pVC0396 and pVC0289, and derivative of pBluescript KS+ in which the bla (Amp$^r$) gene has been replaced were compared with the neo gene. $E.$ $coli$ DH5α containing either pVC0396 or pVC0289 was grown in LB to stationary phase and plasmid DNA was isolated, linearized with HindIII, and analyzed by agarose gel electrophoresis. Comparison of the relative amount of plasmid DNA recovered from equal masses of cells indicates that pVC0396 yields about 2-fold more DNA than pVC0289.

Although high copy number plasmids increase the potential DNA yield from bacterial culture, they also impose a significant metabolic stress on the host cell, which can reduce growth rates relative to plasmid-free cells. Because the copy number of pMM1 and pVC0396 is temperature sensitive, cells can be grown initially at 30° C. to minimize deleterious effects of high copy, and then shifted to 37° C. or 42° C. to induce high copy number to give maximal plasmid yield. $E.$ $coli$ DH5α containing pVC0396 was grown in LB at 30° C. to an $OD_{600}$ of about 0.1. A portion of the culture was then shifted to 37° C., while the remainder was maintained at 30° C. After growth was complete, equal masses of culture were harvested and the plasmid DNA recovered. Comparison of the relative amounts of DNA demonstrates that the temperature shift results in a significant amplification of copy number.

Plasmid pVC0396 contains the neo gene of Tn5, which permits selection for the plasmid in $E.$ $coli$ using kanamycin. This is an advantage over ampicillin resistant gene therapy vectors for several reasons. Ampicillin resistant cells secrete β-lactamase, inactivating the antibiotic in the medium. This leads to the well known feeding effect, which permits plasmid-free cells to survive because the plasmid containing cells have degraded the antibiotic. Kanamycin resistant cells inactivate the antibiotic intracellularly, so there is no feeding effect. As a result, kanamycin is more effective at preventing accumulation of plasmid-free cells during fermentation.

A larger concern relates to the clinical importance of the antibiotics. Some patients are known to be highly allergic to small quantities of β-lactams. Thus, use of ampicillin during production of gene therapy plasmids raises the risk that the final product may be contaminated with ampicillin and unsuitable for use by allergic patients. Furthermore, β-lactams are widely used in the clinic for therapeutic purposes. Widespread use of gene therapy plasmid containing β-lactamase genes could conceivably increase the existing problems with antibiotic resistant bacteria. The use of the neo gene addresses these concerns, since kanamycin does not elicit the type of allergic response sometimes seen with β-lactams, and the more limited clinical applications of kanamycin and related antibiotics provide less concern about potentially resistant bacteria. A final advantage is that the neo gene has previously been used in several human gene therapy studies with no apparent negative effects (Recombinant DNA Advisory Committee Data Management Report, December, 1994, $Human$ $Gene$ $Therapy$ 6:535–548).

The pMM1 origin and the neo gene of pVC0396 are oriented divergently to prevent transcription of neo traversing into the origin. Previous studies with ColE1 derivatives and related plasmids have shown that read-through transcription from neighboring elements into the plasmid origin often leads to plasmid instability and/or reduced copy number (Engels and Meyer, $Biotechniques$ 14:324–325 (1993)). The relative orientation of ori and neo in pVC0396 avoids this problem. Situated between ori and neo is the polylinker sequence from pBluescript KS+. This sequence is provided to permit easy insertion of expression elements such as promoters, therapeutic genes, etc. All of the sites that are unique to this sequence in pBluescript KS+ are also unique in pVC0396, with the exception of PstI and EagI. This provides a total of 17–23 unique sites in the multicloning sequence that can be used for inserting expression elements or previously construction nucleic acid cassettes.

Separating the multicloning sequence and the neo gene is a fragment derived from pKK223-3 (Brosius and Holy, $Proc.$ $Natl.$ $Acad.$ $Sci.$ $USA$ 81:6929–6933 (1984)), containing the strong transcriptional terminators from the $E.$ $coli$ rrnB operon. These terminators are intended to ensure that transcription from the neo gene does not read through into eukaryotic genes that may be cloned into the multicloning sequence. Inadvertent expression of cloned eukaryotic genes in $E.$ $coli$ can sometimes be very inhibitory to cell growth (Brosius, $Gene$ 27:161–172 (1984); Chen, et al., $Gene$ 130:15–22 (1993)). This feature of pVC0396 helps avoid this problem.

All of the elements of pVC0396 are separated from one another by unique restriction sites (see FIG. 1). This feature serves two purposes. First, these sites can be used to insert additional functional elements when desired. Such elements might include partitioning loci to enhance the segregational stability of the plasmid in the absence of selection (Hiraga, $Ann$ $Rev.$ $Biochem.$ 61:283–306 (1992); Williams and Thomas, $J.$ $Gen.$ $Microbiol.$ 138:1–16 (1992)) or multimer resolution loci to help maintain the plasmid in the monomeric state (Eberl, et al., $Mol.$ $Microbiol.$ 12:131–141 (1994); Cornet, et al., $J.$ $Bacteriol.$ 176:3188–3195 (1994); Summers, et al., $Mol.$ $Gen.$ $Genet.$ 201:334–338 (1985)). Secondly, these sites are designed to create a modular plasmid whose individual elements can be easily removed, replaced, or altered. This is an important feature, because there are many possible plasmid modifications that may become necessary for specific applications. The flexibility afforded by the modular design will greatly facilitate such modifications.

Operator Selection

While one reason for selection of the neo gene was based on potential use in humans, alternative selection systems are desirable for plasmids that will ultimately be marketed for human use. This would eliminate concerns that the neo gene might be transferred to potential pathogens, rendering them resistant to aminoglycoside antibiotics. Elimination of the neo gene from the plasmid is also desirable since it will substantially reduce the size of the plasmid. Smaller plasmids are intrinsically easier to manipulate and purify, and provide less opportunity for unanticipated interactions with expression elements that may be inserted during the construction of a gene therapy plasmid. Furthermore, removing the antibiotic resistance coding region may reduce the metabolic stress on the cell by eliminating high level transcription and translation of a plasmid-encoded gene present at high copy number in the cell.

Instead of antibiotic resistance genes, other selection systems have been used. Systems using the ssb gene or suppressor tRNA genes as described above have certain disadvantages. The first approach suffers from the requirement that a functional gene such as ssb must be present on the plasmid, and must be deleted from the host. This requires specially designed host strains which must be constructed or otherwise obtained and may be difficult to obtain with the desired genetic background. Furthermore, the presence of ssb or another gene on the plasmid still results in synthesis of mRNA and protein from a high copy number gene, consuming substantial metabolic energy and reducing growth rate. Also, replacing an antibiotic resistance gene with ssb does not reduce plasmid size as much as desired. Finally, the ssb gene may not be significantly safer for human use than the neo gene, since the product of ssb is highly active in nucleic acid metabolism. Inadvertent expression of ssb in cells of a human patient could have unanticipated and undesirable effects.

The second approach has certain advantages, in that the tRNA selectable marker is quite small, <200-bp, and does not encode a protein. Use of this system is also problematic, however. As before, specially modified host strains are required. The presence of additional suppressor tRNA genes in the host may be a problem. It is generally necessary to use simultaneous selection for several antibiotic resistance genes to achieve sufficiently stringent selection. Furthermore, it is difficult to engineer the system to permit independent selection of different plasmids using different antibiotics. Finally, although the selectable tRNA gene on the plasmid does not encode protein, it nevertheless encodes a functional tRNA product, which raises the concerns over metabolic energy consumption when cloned on a high copy number plasmid, as well as the potential consequences of inadvertent expression in a human patient.

The popularity of antibiotics in molecular biology is a testament to the ease with which they may be used to select and maintain plasmids in bacteria. Antibiotics are generally cheap and effective, and are relatively nontoxic to humans. These are critical concerns when considering that fermentation on a scale of hundreds or thousands of liters is likely for the production of nonviral gene therapy products that progress beyond Phase I clinical trials. Thus, it would be useful to select for plasmid maintenance using antibiotics. However, it would also be desirable to avoid incorporating antibiotic resistance genes in the gene therapy plasmid itself, because of concerns over disseminating of antibiotic resistance in the environment, and because antibiotic resistance genes generally add about 1 kb or more to the plasmid size.

The present invention sets forth a system in which antibiotic resistance genes are incorporated into the *E. coli* chromosome under the control of heterologous promoter/repressor systems. In the absence of a plasmid, the chromosomally encoded repressor prevents transcription of the integrated resistance gene, and the host is sensitive to antibiotic. To induce expression of the resistance gene, a plasmid is introduced that contains binding sites, or operators, recognized by the repressor protein. If the plasmid is present in high copy number, and the repressor gene is encoded by a single copy chromosomal gene, virtually all of the repressor protein will bind to sites on the plasmid molecules. This leaves little or no repressor to block transcription of the resistance gene, which renders the cells resistant to antibiotic.

This phenomenon, where an operator sequence present on a high copy number plasmid derepresses a chromosomal operon, is called repressor titration. It has been used by a number of investigators to study repression and derepression of bacterial operons. To date, more than 20 repressor operator systems in *E. coli*, Staphylococcus, Bacillus, Klebsiella, Streptomyces, Saccharomyces, and Salmonella, as well as in plasmids such as R1 and transposons such as Tn10, have been shown to be subject to repressor titration (Simons, et al., *Proc. Natl. Acad. Sci. USA* 81:1624–1628 (1981); Straigier, et al., *J. Bacteriol.* 156:1198–1203 (1983); Oskouian and Stewart, *J. Bacteriol.* 169:5459–5465 (1987); Danner, *Gene* 44:193–199 (1986); Bautista and Graham, *Gene* 87:201–208 (1989); Mata-Gilsinger, et al., *Genetics* 105:829–842 (1983); Fritz, et al., *EMBO J.* 2:2129–2135 (1983); Brikun, et al., *Genetika* 25:1717–1724 (1989); Hammer, et al., *Mol. Gen. Genet.* 237:129–133 (1993); Barker, et al., *Gene* 13:89–102 (1981); Wray and Reznikoff, *J. Bacteriol.* 156:1188–1191 (1983); Benner-Luger and Boos, *Mol. Gen. Genet.* 214:579–587 (1988); Fujita and Fujita, *Nucleic Acids Res.* 14:1237–1252 (1986); Latour and Weiner, *Nucleic Acids Res.* 16:6339–6352 (1988); Kilstrup, et al., *Eur. J. Biochem.* 176:421–429 (1988); Giza and Huang, *Gene* 78:73–84 (1989); Salmaron, et al., *Mol. Cell. Biol.* 9:2950–2956 (1989); Aslandis and Schmitt, *J. Bacteriol.* 172:2178–2180 (1990); Naik and Hassan, *Proc. Natl. Acad. Sci. USA* 87:2618–2622 (1990); Huong, et al., *J. Bacteriol.* 172:4392–4398 (1990); Brikin, et al., *Mol. Gen. Mikrobiol. Virusol.* 6:7–11 (1990); Sogaard-Andersen, et al., *Mol. Microbiol.* 4:1595–1601 (1990); Jensen, et al., *J. Mol. Biol.* 236:1299–1309 (1994); Linder, et al., *Microbiology* 140:753–757 (1994); Virolle and Gagnat, *Microbiology* 140:1059–1067 (1994); Osuna, et al., *J. Bacteriol.* 176:5525–5529 (1994); and Windass and Brammer, *Mol. Gen. Genet.* 172:329–337 (1979)).

In some instances, this phenomenon has been used to screen for recombinant plasmids, based on insertional inactivation of a lac operator sequence cloned on a multicopy plasmid, (Danner, *Gene* 44:193–199 (1986); Bautista and Graham, *Gene* 87:201–208 (1989)). The system described here adapts repressor titration for use in selecting for the introduction or continued presence of a plasmid.

The advantage of this system is that it enables antibiotics to be used to select for a plasmid, based only on the presence of a small operator sequence on the plasmid itself. The antibiotic resistance gene is located on the host chromosome, posing essentially no risk that the gene will be transferred to the patient or to a pathogen during therapeutic use. The size of the selectable sequence on the plasmid can be as small as about 20 bp. Furthermore, two or more independent operator selection systems can operate at the same time in the same cell, either to co-select for two compatible plasmids, or to impose double selection on a single plasmid. These features are illustrated below.

Construction of Plasmids and Host Strains for Operator Selection

Figure 3:
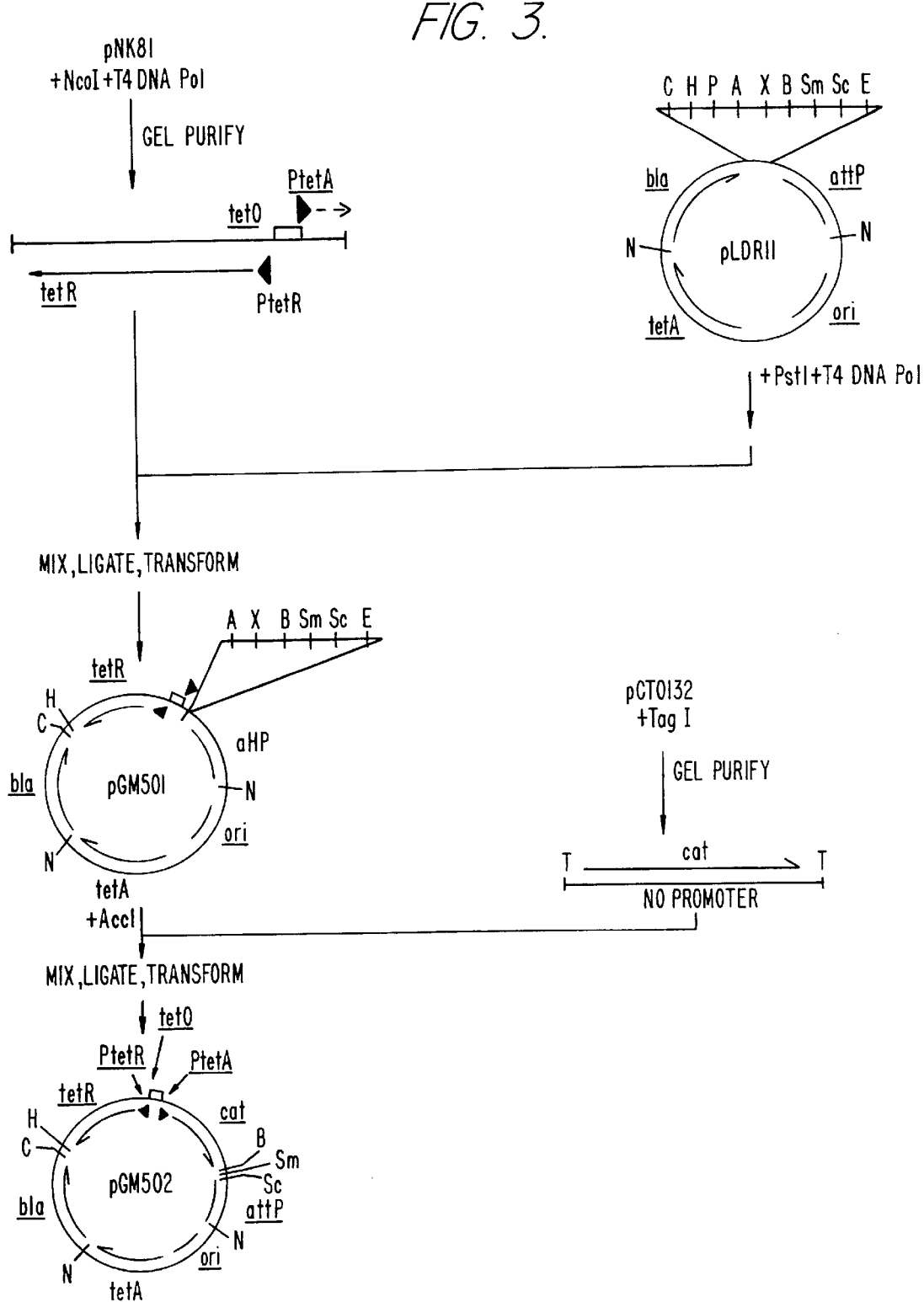
FIG. 3 represents a schematic of the construction of pGM502.
Figure 4:
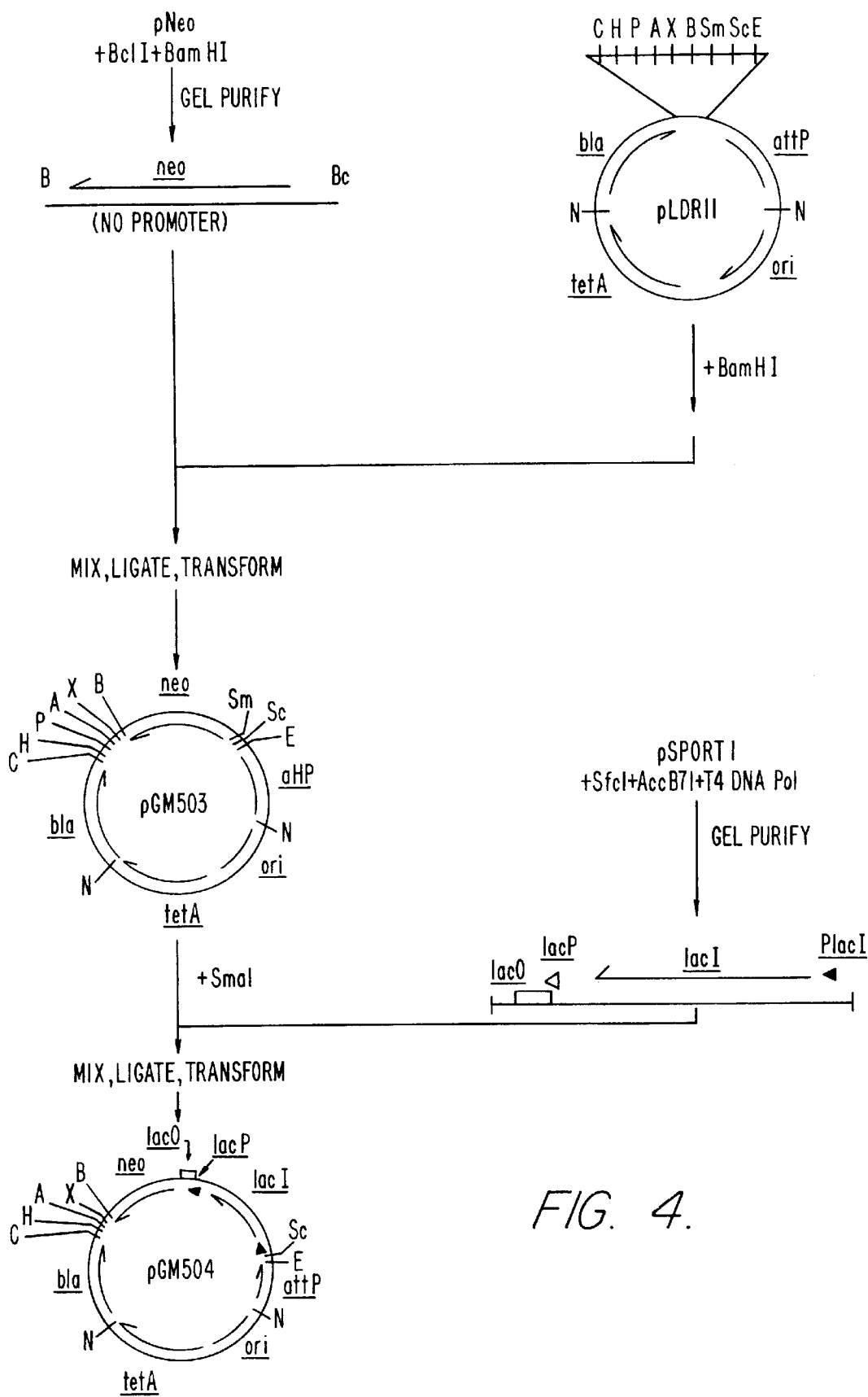
FIG. 4 represents a schematic of the construction of pGM504.
Figure 5:
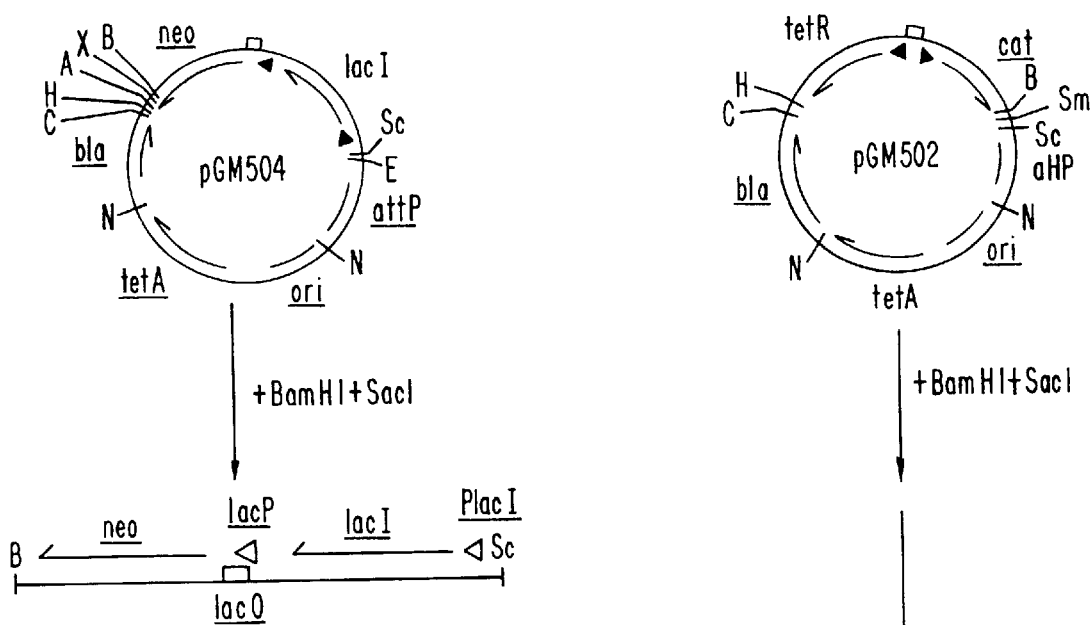
FIG. 5 represents a schematic of the construction of pGM505.
Figure 5:
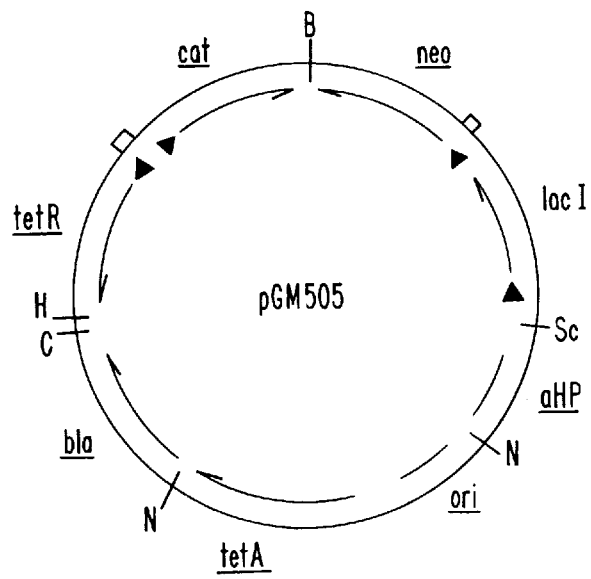

FIGS. 3, 4, and 5 describe the construction of plasmids pGM502, pGM504, and pGM505, respectively. For the construction of pGM502, abbreviations for restriction enzyme sites are as follows: C. ClaI; H. HindIII; P. PstI; A. AccI; X. XbaI; B BamHI; Sm. SmaI; Sc. SacI; E. EcoRI; N. NotI; T. TaqI. Gene symbols are as follows: tetR, tetracycline repressor gene; $P_{tetR}$, tetracycline repressor gene promoter; tetO, tetracycline operator (binding site for TetR protein); $P_{tetA}$, tetracycline resistance gene promoter; tetA, tetracycline resistance gene; attP, phage lambda attachment sequence; cat, chloramphenicol resistance gene. Additional gene symbols can be found with the description of FIG. 2, above.

For the construction of pGM504, restriction enzyme sites and gene symbols are described with FIGS. 2 and 5 above.

Additional symbols are: Bc, BclI site; lacI, lactose operon repressor gene from E. coli; lacP, lactose operon promoter; PlacI, lacI gene promoter; lacO, lactose operon operator (binding site for LacI repressor protein.

For construction of pGM505, gene symbols and restriction site abbreviations are described above as with FIGS. 2, 3 and 4.

All three plasmid are based on plasmid pLDR11, a plasmid designed by Diederich, et al., *Plasmid* 28:14–24 (1992), as part of a system to facilitate integration of cloned DNAs into the *E. coli* chromosome. Plasmid pGM502 (FIG. 3) contains the cat gene under the control of the Tn10 tetA promoter ($P_{tetA}$), which is negatively regulated by the tetR repressor gene. The regulatory system of tetT and $P_{tetA}$ has been used by others to achieve tightly regulated expression of a variety of genes in prokaryotic and eukaryotic systems. In the absence of tetracycline, the TetR repressor protein binds the operator sequence tetO, blocking transcription from $P_{tetA}$. $P_{tetA}$ can be derepressed by adding anhydrotetracycline, a tetracycline analog, which binds to and inactivates TetR. This leads to expression of the cat gene downstream of $P_{tetA}$.

Plasmid pGM504 (FIG. 4) contains the Tn5 neo gene under the control of the *E. coli* lacI-lacOP system. In this system, the LacI repressor blocks transcription from the lac promoter, lacP, by binding to the operator lacO. Addition of IPTG prevents binding of LacI to lacO. This derepresses lacP, permitting transcription of the downstream neo gene. Plasmid pGM505 (FIG. 5) contains both of these systems cloned into a single plasmid.

In order to transfer the appropriate DNA segments from pGM502, pGM504, and pGM505 to the *E. coli* chromosome, the procedure of Diederich, et al., *Plasmid* 28:14–24 (1992) was followed. This procedure is summarized in FIG. 6. For the construction of *E. coli* GMS001, plasmid pGM502 was digested with NotI and ligated under conditions where unimolecular reactions predominate, yielding the two products shown. *E. coli* DH5α containing pLDR8 was transformed under conditions where a transformed cell receives at most one ligated DNA. Cells which were transformed with the tetA/ori fragment of pGM502 were screened out based on tetracycline resistance and discarded. Transformants were incubated at 37° C. to induce expression of int, leading to integration of the attP-containing fragment of pGM502 into the *E. coli* chromosomal attB site. Simultaneously, the elevated incubation temperature inactivates replication of pLDR8, which is lost from the cell. The resulting strain, which contains the large NotI fragment of pGM502 integrated at the attB site of the chromosome, was designated *E. coli* GMS001. Gene symbols are denefid as discussed with FIGS. 2, 3, and 4.

Figure 6A:
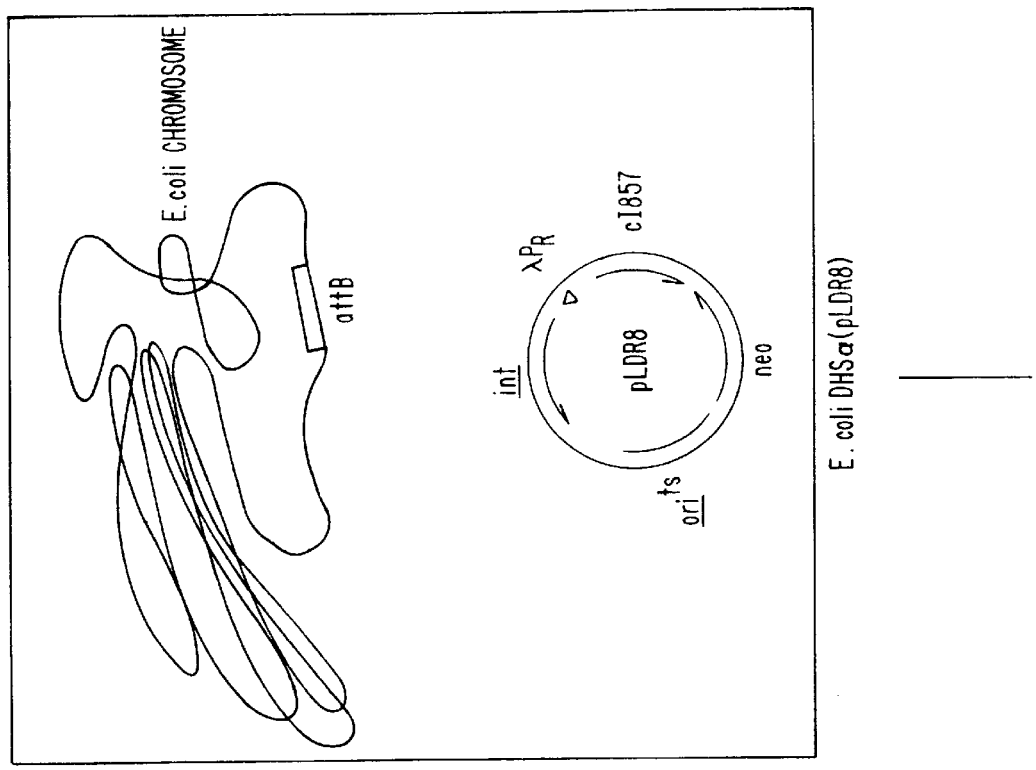
FIG. 6 represents a schematic of the construction of E. coli GMS001.
Figure 6A:
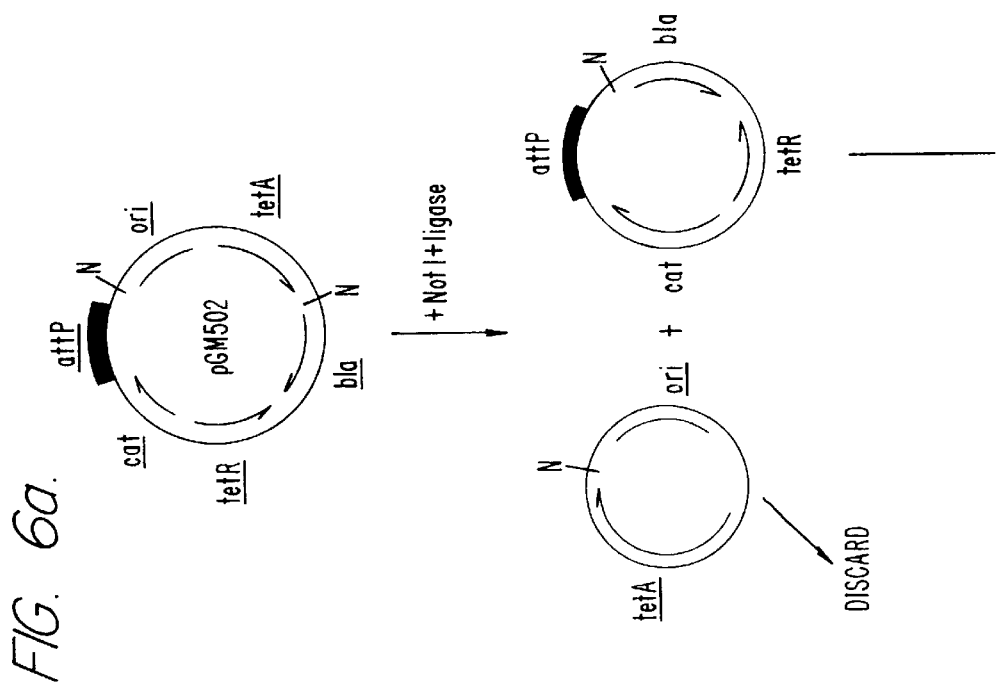
Figure 6B:
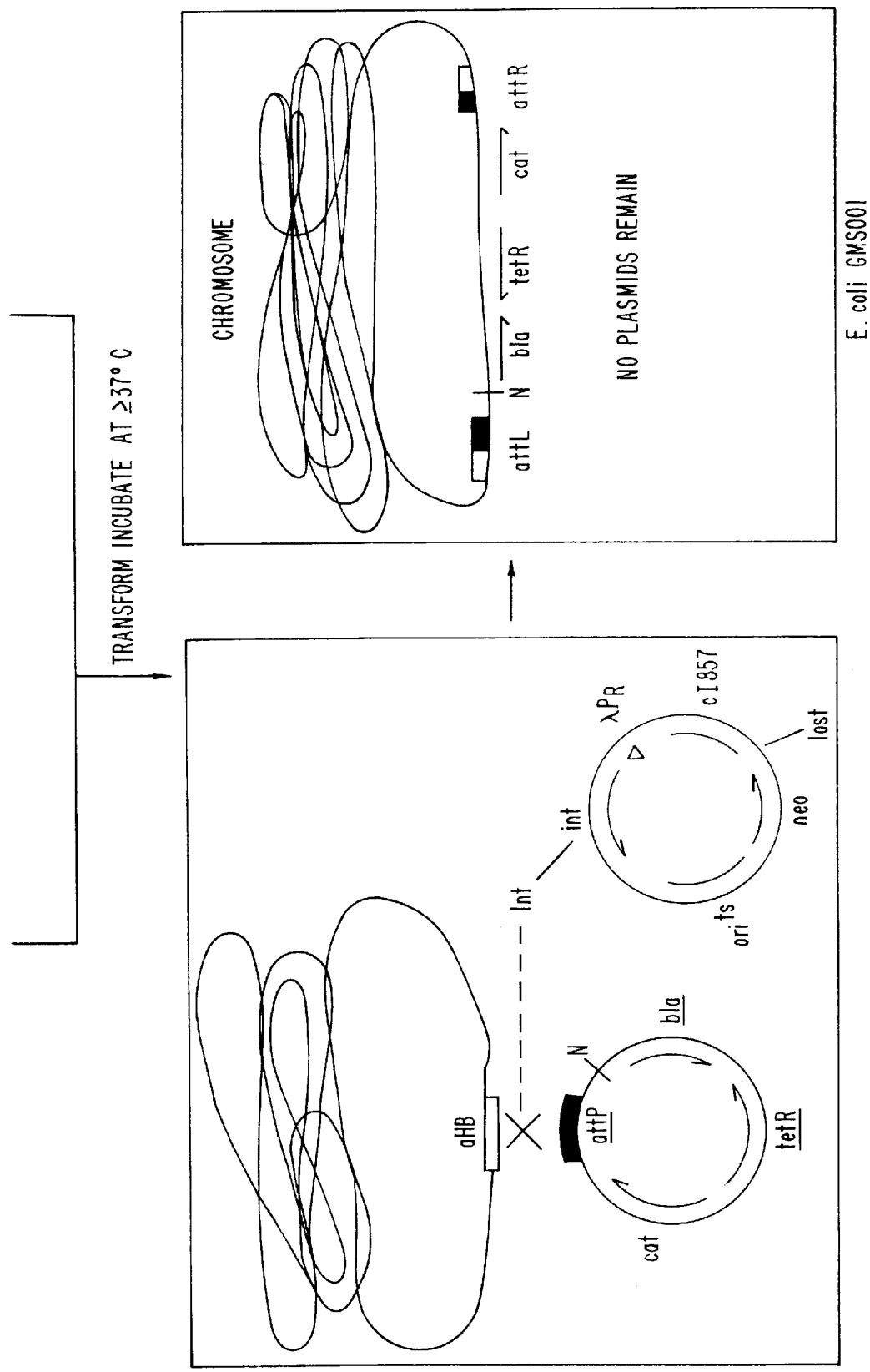

As noted above, pGM502 was digested with NotI, and recircularized under conditions where the majority of ligation events are unimolecular. This results in the two products are shown in FIG. 6. The desired product contains the bla gene, attp, and the repressor/promoter/resistance gene cassette. The remaining ligation product consists of the plasmid replication origin and the tetracycline resistance gene (tetA).

The ligation mixture was transformed into *E. coli* DH5α (pLDR8) under conditions where cotransformation by both of the ligation products of the NotI-digested pGM502 was unlikely. The transformed cells were then incubated at 37° C. This has two effects. First, it inactivates the product of the cI857 gene of pLDR8, inducing expression of the int gene. Expression of Int catalyzes integrative recombination between attp-containing DNA and the chromosomal attB site, as shown. At the same time, growth at 37° C. prevents replication of the temperature sensitive pLDR8, which is quickly lost from the cell. The result is a derivative of *E. coli* DH5α designated *E. coli* GMS001 that contains the large NotI fragment of pGM502 integrated at the attb site of the chromosome. Appropriate clones can be selected using ampicillin, due to cointegration of the bla gene. $Amp^r$ colonies were then screened for tetracycline sensitivity, to ensure loss of the tetA-containing fragment of pGM502. These were further characterized by plasmid analysis and by southern blotting to confirm; (a) the expected structure of the integrated DNA; (b) the absence of pLDR8 and any other non-integrated plasmid DNA; and (c) the absence of the origin and tetracycline resistance gene fragment of pLDR11. The same strategy and protocol was used to generate *E. coli* GMS002 from pGM504, and to generate GMS003 from pGM505.

To confirm that the integrated DNA fragments were functional, the antibiotic resistance levels of each strain under conditions where the resistance gene should be either repressed or derepressed were compared. In the first study, *E. coli* GMS001, GMS002, and GMS003 were grown in LB at 37° C. to mid log phase. Aliquots of each culture were diluted and plated on LB plates containing the additives shown in Table 2 below.

TABLE 2

Resistance of *E. coli* strains GMS001, GMS002, and GMS003 to chloramphenicol and kanamycin in the absence and presence of chemical inducers.

| plate additive | GMS001 | GMS002 | GMS003 |
| --- | --- | --- | --- |
| none | | | |
| y | + | + | + |
| amp | + | + | + |
| cam | − | − | − |
| cam + tet | + | − | + |
| kan | − | − | − |
| kan + IPTG | − | + | + |
| cam + kan | − | − | − |
| cam + kan + tet | − | − | − |
| cam + kan + IPTG | − | − | − |
| cam + kan + tet + IPTG | − | − | + |

Figure 8A:
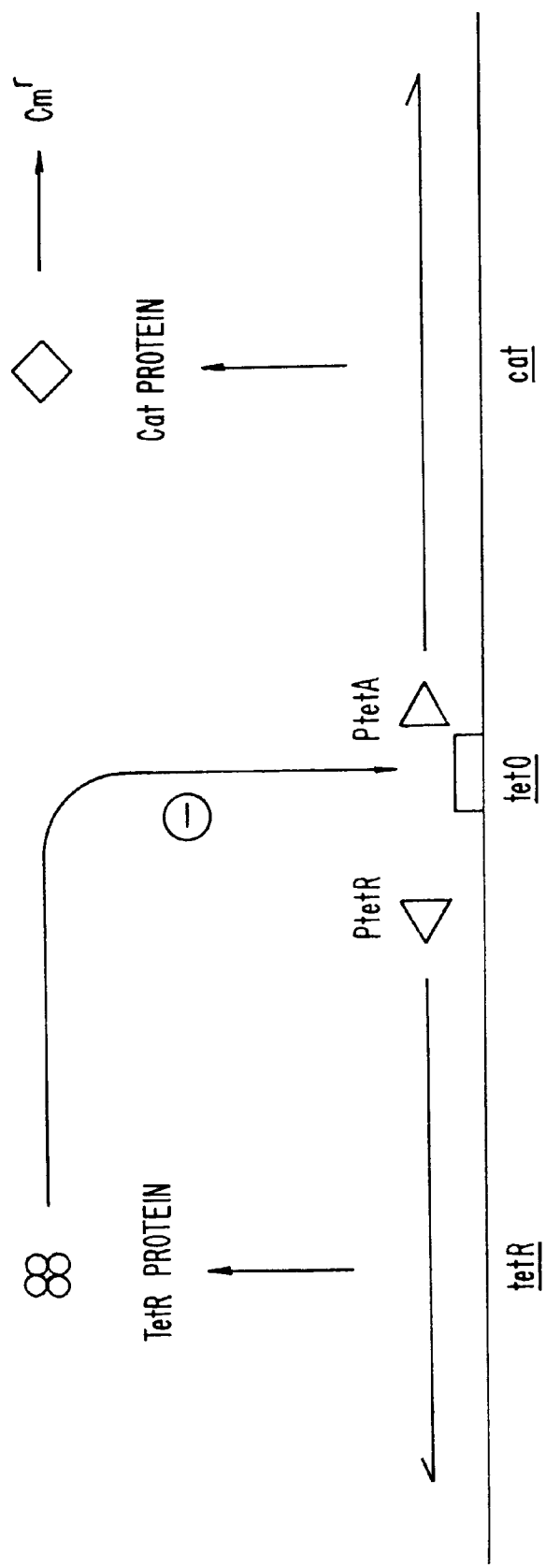
FIG. 8 represents a schematic drawing of the operator selection mechanism.
Figure 8B:
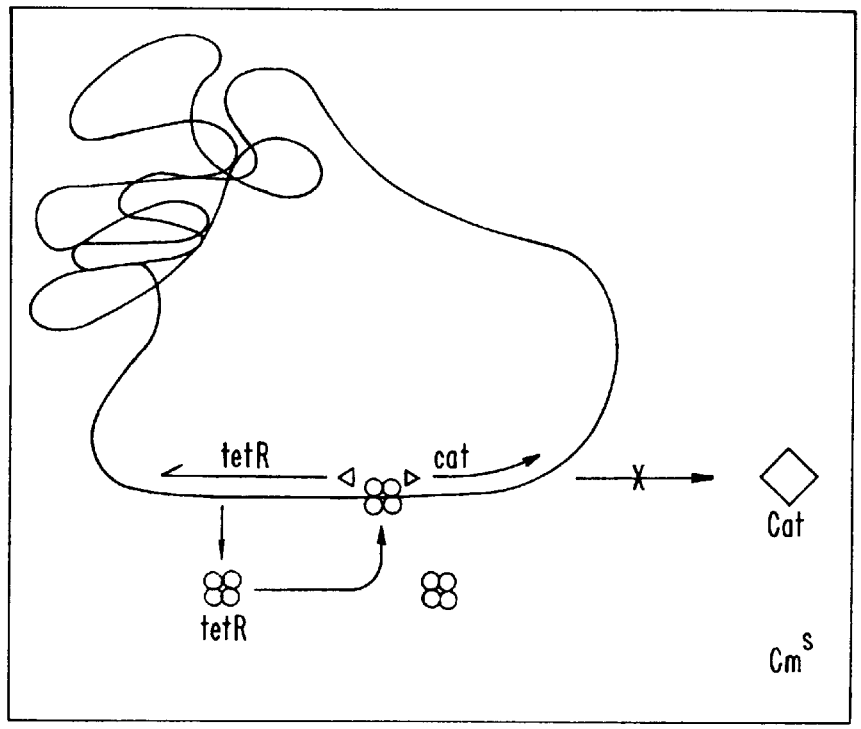
Figure 8C:
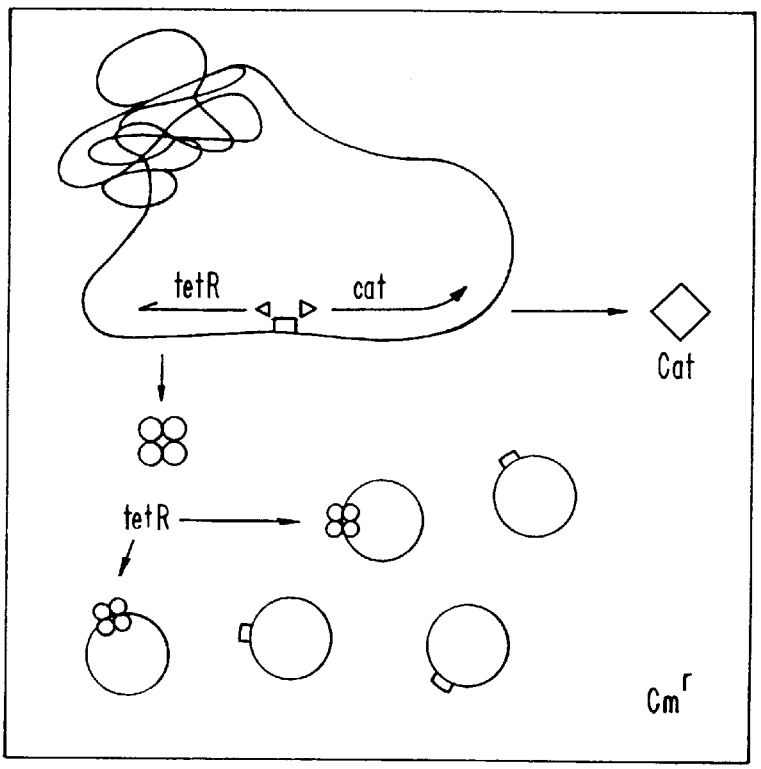

After incubation overnight, growth of single colonies was scored. As shown in Table 2, all three strains were resistant to ampicillin, due to the presence of a constitutive bla gene integrated in each cell (see FIG. 8). GMS001 was sensitive to chloramphenicol alone, but was resistant to chloramphenicol in the presence of anhydrotetracycline, which derepresses the $P_{tetA}$ promoter upstream of cat. Similarly, *E. coli* GMS002 was kanamycin sensitive in the absence of IPTG, but kanamycin resistant in the presence of IPTG. Addition of IPTG derepresses the lacP promoter, inducing expression of the neo gene. *E. coli* GMS003 was resistant to chloramphenicol in the presence of anhydrotetracycline, and to kanamycin in the presence of IPTG, as expected. Moreover, GMS003 was able to grow in the presence of both chloramphenicol and kanamycin, but only when both tetracycline and IPTG were added to derepress both systems. These results demonstrate that the two selection systems can operate simultaneously, with no spurious interference or cross-reactivity. Similar studies were conducted in liquid medium with similar results demonstrating that the appropriate selection is possible with each strain, either on solid or liquid media.

Construction and Testing of Plasmids Containing Selectable Operator Sequences

Figure 7:
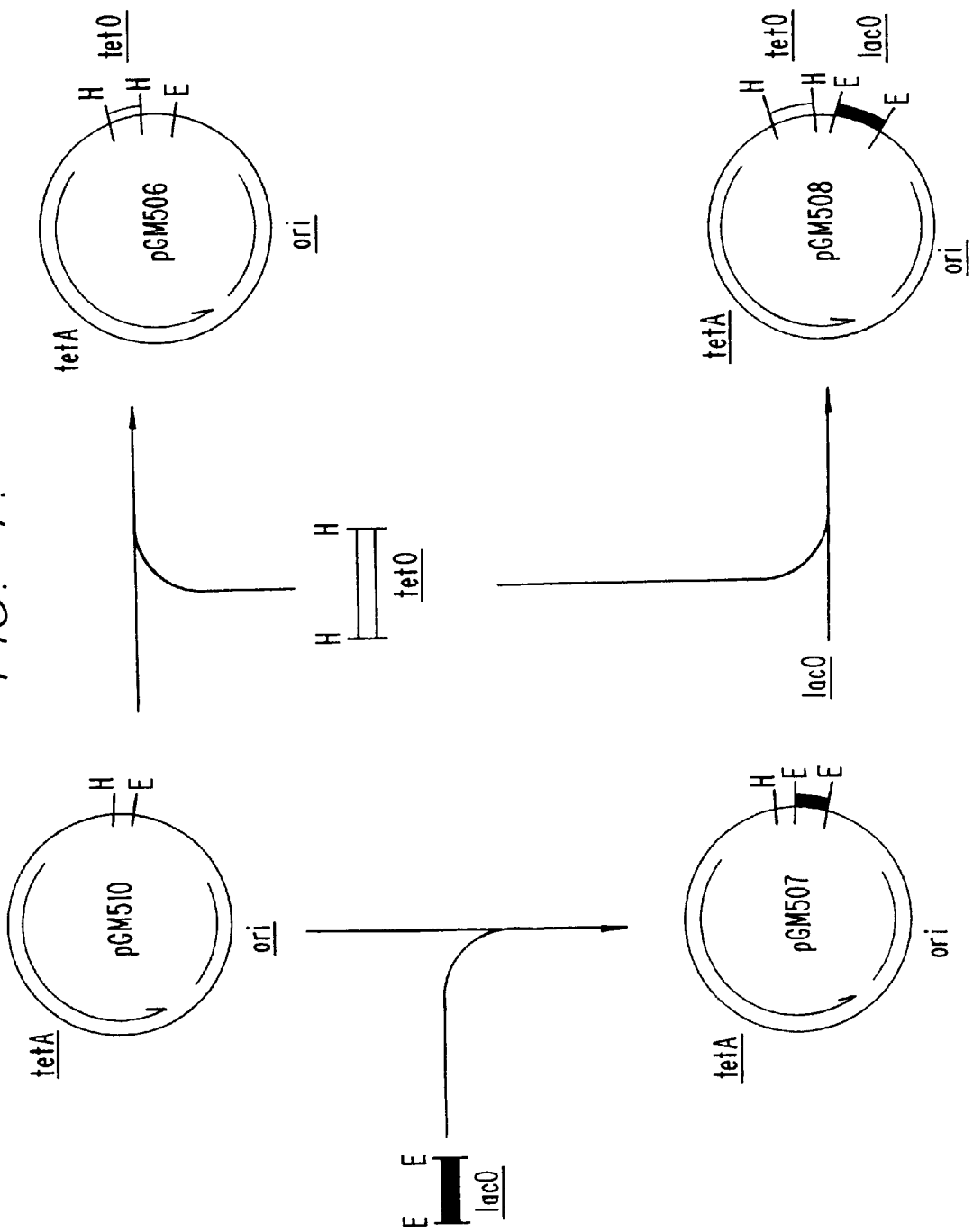
FIG. 7 represents a schematic of the construction of pGM506, pGM507, and pGM508.

To test whether the antibiotic resistance genes integrated into the above *E. coli* strains could be induced by plasmids carrying the appropriate operator sequences, the plasmids described in FIG. 7 were constructed. For the construction of pGM506, pGM507 and pGM508, plasmid pGM510 is a derivative of pUC18 which lacks the bla (Amp$^r$) and the lacO elements and carries the gene for tetracycline resistance. A synthetic fragment containing the tetO operator flanked by an HindIII site was prepared by annealing complementary oligonucleotides of the following sequence: 5'-AGC-TTC-TCT-ATC-AGT-GAT-AGA-GA-3' (SEQ ID NO. 3) and 5'-AGC-TTC-TCT-ATC-ACT-GAT-AGA-GA-3' ((SEQ ID NO. 4). The annealed oligonucleotide was ligated to HindIII-digested pGM510 to give pGM506. Similarly, a synthetic fragment containing the lacO operator flanked by EcoRI sites was prepared by annealing a self-complementary oligonucleotide with the sequence 5'-AAT-TCA-ATT-GTG-AGC-GCT-CAC-AAT-TG-3' (SEQ ID NO. 5). The annealed lacO oligo was ligated to EcoRI digested pGMS10 to give pGM507. Plasmid pGM508 was prepared by inserting the tetO operator oligo into the HindIII site of pGM507, as shown. Gene symbols and restriction site abbreviations are defined with the description of FIGS. 2, 3, and 4.

All three plasmids contain the pUC replication origin, specifying high copy number, and the tetracycline resistance gene. PGM506 contains a synthetic 19-bp tet operator consensus sequence. PGM507 contains a 21-bp synthetic lac operator consensus sequence, while pGM508 contains both operators. Each of these plasmids was transformed into either GMS001, GMS002, or GMS003 and tested for growth in the presence of antibiotic selection. The results are presented in Table 3.

TABLE 3

Antibiotic resistance of GMS001, GMS002, and GMS003 containing plasmids pGM506, pGM507, or pGM508.

| host | plasmid | tet | cam | kan |
|---|---|---|---|---|
| GMS001 | pGM506 | + | + | − |
| " | pGM507 | + | − | − |
| " | pGM508 | + | + | − |
| GMS002 | pGM506 | + | − | − |
| " | pGM507 | + | − | + |
| " | pGM508 | + | − | + |
| GMS003 | pGM506 | + | + | − |
| " | pGM507 | + | − | + |
| " | pGM508 | + | + | + |

The observed resistance of each combination of strain and plasmid is as predicted. Plasmid pGM506, carrying the tet operator, derepresses expression of cat in GMS001, leading to chloramphenicol resistance. This is shown schematically in FIG. 8. In general, the following is the working mechanism of operator selection. "A" represents the regulatory circuit for the control of cat expression by tetR. The regulatory circuit shown in "A" is integrated into the E. Coli chromosome. In the absence of plasmids, the tetR repressor protein, product of the tetr gene, binds to tetO and inhibits transcription from $P_{tetA}$ is depressed, expression cat and rendering the cell resistant to chloramphenicol. Gene symbols are defined as described above with FIGS. 2, 3, and 4.

Similarly, pGM507, carrying the lac operator, derepresses expression of neo in GMS002, leading to kanamycin resistance. Each of these plasmids is also able to derepress the appropriate antibiotic resistance gene in GMS003. Furthermore, pGM508, carrying both the tet and the lac operator, derepresses cat in GMS001 and GMS003, and neo in GMS002 and GMS003. These results demonstrate that about 20-bp long operator sequences can be used as selectable elements to ensure maintenance of plasmids in E. coli.

The operator selection scheme has a number of advantages. First, by moving the antibiotic resistance gene to the host chromosome, there is no concern about transferring the gene to human patients. Second, the plasmid selectable markers are operator sequences of only about 20-bp, as compared to about 800-bp for antibiotic resistance genes. Furthermore, the operator sequences on the plasmid have no coding capacity.

Without coding capacity there is no possibility that a prokaryotic protein might be inadvertently expressed in a human, or other eukaryotic system, since no prokaryotic coding sequence is present. In addition, elimination of the coding sequence is beneficial in E. coli as well. High copy number plasmids carrying functional genes often produce high levels of protein from those genes due to the gene dosage effect. This can consume a considerable amount of metabolic energy and reduce growth rates (Brosius, Gene 27:161–172 (1984); Chen, et al., Gene 130:15–22 (1993); Bentley, et al., Biotechnol. Bioeng. 35:668–681 (1990); Park, et al., Biotechnol. Bioeng. 37:297–302 (1991); Peretti and Bailey, Biotechnol. Bioeng. 24:316–328 (1987)).

Operator selection permits construction of selectable plasmids that do not contain any bacterially expressed coding sequences. This reduces the metabolic drain on the host cell, and permits higher growth rates and less tendency for plasmid-free cells to overgrow the culture. These advantages make operator selection very suitable for use in human gene therapy constructs, from the standpoints of both safety and utility. The lack of cross resistance between two independent selection systems, as demonstrated with pGM506 and pGM507 in GMS003, permits simultaneous selection for two different, compatible plasmids carrying different operator sequences. Double selection can be imposed on a plasmid carrying two operators, as for pGM508 in GMS003, to increase the stringency of selection. Finally, this system can easily be adapted to other repressor/promoter/operator systems (such as lambda cI/$P_R$/$O_R$) and other antibiotic resistance genes (such as tetracycline, erythromycin, etc). New operator selection systems can easily be integrated into the E. coli chromosome using the lambda integration system of Diederich, et al., Plasmid 28:14–24 (1992). Thus, a variety of E. coli strain backgrounds can be quickly and easily adapted for use in operator selection.

Use of Operator Selection in Derivatives of pVC0396

In addition to the above uses, the operator selection of the present invention also allows a large number of plasmid constructs to be tested. Such testing is important to optimize gene therapy plasmids so as to move into production mode for clinical trials. Multiple combinations of therapeutic genes and regulatory elements must often be constructed and evaluated. Introduction of therapeutic genes and regulatory elements into a plasmid may require multiple cloning steps. During each step, appropriate plasmids must be identified, grown in culture, and purified. It may also be necessary to use different E. coli hosts during the construction. These operations may be hampered if operator selection is the only available means to select for appropriate transformants and for plasmid maintenance.

Ideally, preliminary plasmid constructions might use a backbone that contains a complete antibiotic resistance gene, such as pVC0396 which contains the neo gene. This would permit selection using kanamycin in any desired E. coli host, without the restrictions of operator selection or other non-antibiotic selection systems. Once a plasmid had been selected as a potential clinical candidate, however, it would be desirable to eliminate the antibiotic resistance gene from the plasmid and use operator selection instead.

Figure 9:
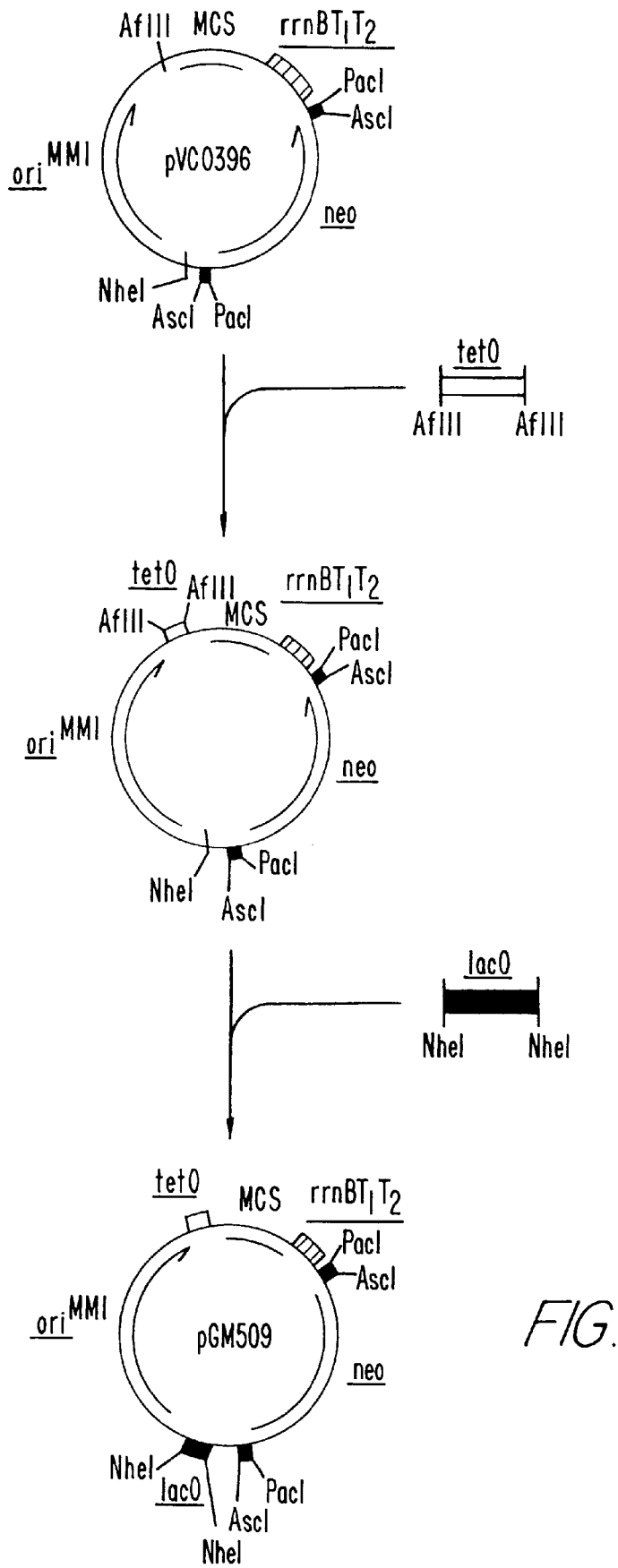
FIG. 9 represents the schematic for the construction of pGM509.

FIG. 9 shows the construction of pGM509, a derivative of pVC0396 containing both the tet and lac synthetic operators. For the construction of pGM509, the tetO and lacO operator sequences were cloned into the AflII and NheI sites, respectively, of pVC0396 in two steps. Oligonucleotide sequences were as follows: tetO, 5'-TTA-AGT-CTC-TAT-CAG-TGA-TAG-AGA-3' (SEQ ID NO. 6) and 5=-TTA-AGT-CTC-TAT-CAC-TGA-TAG-AGA-3' (SEQ ID NO. 7); 5'-TAT-GAA-TTG-TGA-GCG-CTC-ACA-ATT-G-3' (SEQ ID NO. 8) (self-complementary). Gene symbols are defined as discussed within FIGS. 2, 3, and 4.

This plasmid can be selected in any host using kanamycin, due to the presence of the intact, functional neo gene. The synthetic operators also provide the potential for operator selection in *E. coli* GMS001, GMS002, or GMS003. However, in order to benefit from the advantages of operator selection, the neo gene in pGM509 must be removed.

Figure 10A:
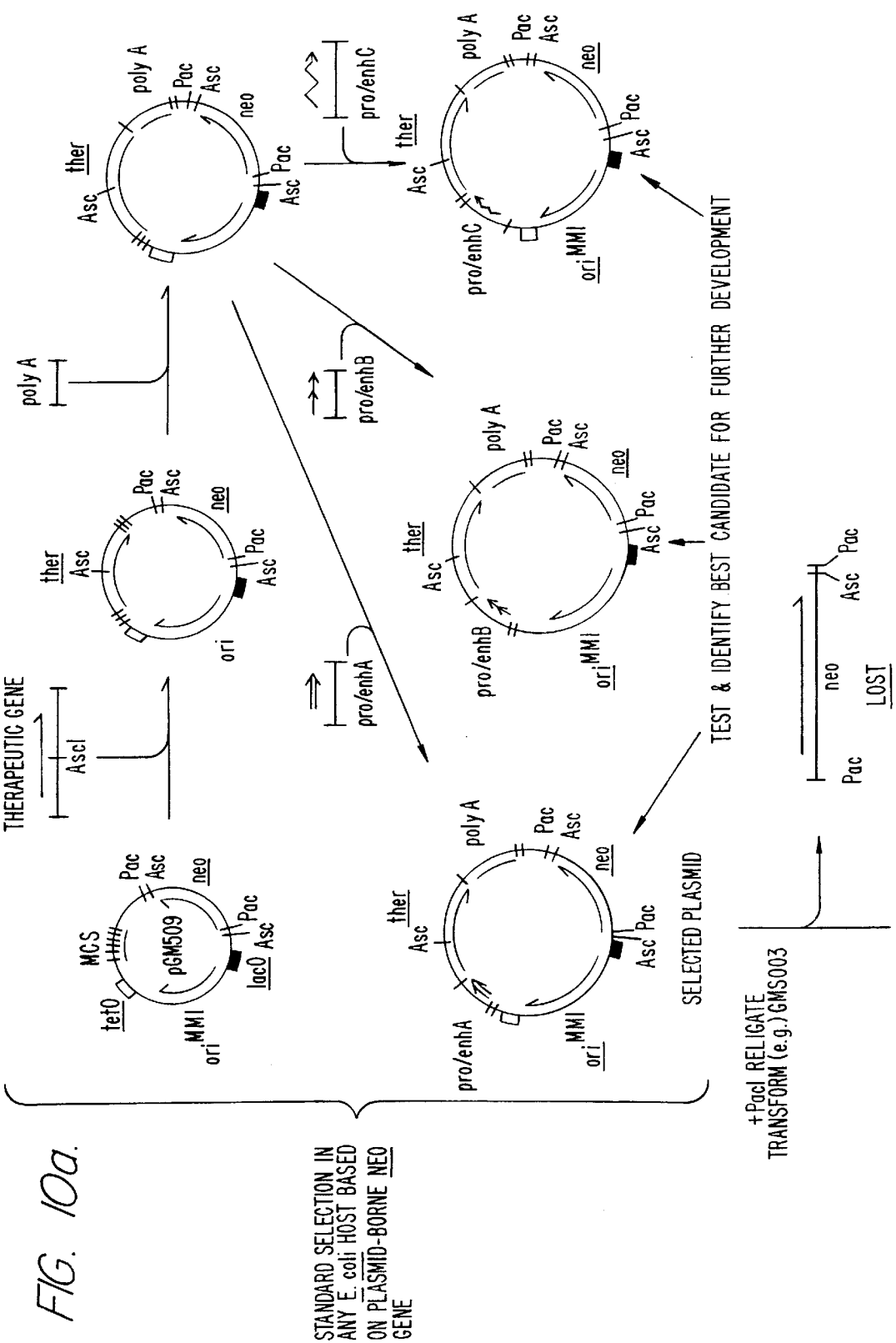
FIG. 10 represents a schematic of the use of pGM509.
Figure 10B:
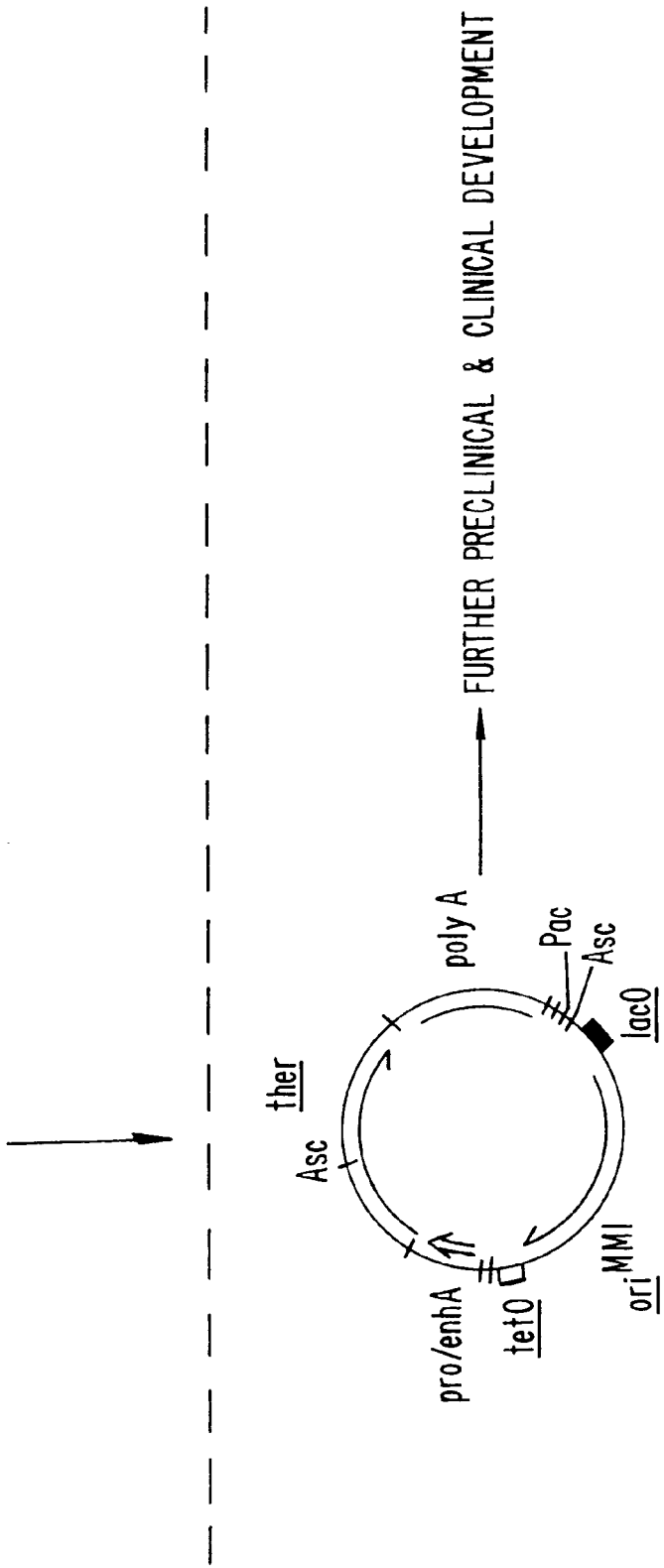

The neo gene in pGM509 (and in pVC0396) is flanked by pairs of AscI and PacI 8-bp restriction sites. FIG. 10 details the method by which pGM509 may be used to achieve the goals described above, namely, selection based on the plasmid-borne neo gene during preliminary research, followed by removal of neo and selection based on the tet or lac operator for potential clinical use. Therapeutic genes and regulatory elements are inserted through a number of steps into the polylinker of pGM509. Plasmids are selected in any *E. coli* host based on the neo gene. Individual plasmids may be screened for expression of the therapeutic gene to select a suitable candidate for further work.

In particular, a variety of cloning steps are used to introduce a potential therapeutic gene, and poly-A signal sequence, and various promoter/enhancer fragments (pro/enh A-C) into the polylinker of pGM509 (labeled MCS in the figure). Throughout these steps, plasmids may be transformed and maintained in any *E. coli* host, with selection for kanamycin resistance based on the plasmid-encoded neo gene. Various tests may be performed to identify which of the candidate plasmids is most suited to additional preclinical and clinical development.

Once a candidate is selected (center left), the plasmid is digested with either AscI or PacI. Because AscI and PacI recognize 8-bp sequences, it is likely that at least one of them will not cut within the expression elements. For example, assuming that the therapeutic gene contains an AscI site, the plasmid is digested with PacI. The large fragment is recircularized to create a derivative that lacks the neo gene, and can be selected by transforming into GMS001, GMS002, or GMS003 (or another host with the appropriate chromosomal modification to support operator selection) and growing in the appropriate antibiotic. This generates a plasmid that contains no antibiotic resistance gene, and no prokaryotic coding sequences, for potential human use.

A similar approach can be used in the case where one of the expression elements contains a PacI site. The same process is applied, except that digestion is with AscI. Note that, due to the relative arrangement of the AscI and PacI sites at each end of the neo gene, digestion with either enzyme, followed by recircularization, leads to an identical backbone sequence containing single AscI and PacI sites upstream of lacO. Thus, the choice of AscI or PacI is irrelevant to the final structure of the plasmid, as long as the chosen enzyme does not cut within the expression cassette region.

One skilled in the art will readily appreciate that the present invention is well adapted to carry out the objects and obtain the ends and advantages mentioned as well as those inherent therein. The plasmids described herein along with the methods, procedures and treatments using such plasmids are presently representative of preferred embodiments, are exemplary and not intended as limitations on the scope of the invention. Changes therein and other uses will occur to those skilled in the art which are encompassed within the spirit of the invention or defined by the scope of the claims.

It will be readily apparent to one skilled in the art that varying substitutions and modifications may be made to the invention disclosed herein within departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

We claim:

1. A plasmid for delivery of a nucleic acid sequence to a eukaryotic cell, comprising:
   (a) a region which regulates plasmid copy number, wherein said region includes an origin of replication sequence; and
   (b) an element providing selection of a prokaryotic host cell containing said plasmid, wherein said selection does not require a transcribed selection gene on said plasmid.

2. The plasmid of claim 1, further comprising a linker region, wherein said linker region includes a multicloning site for inserting a nucleic acid sequence; and
   wherein said element providing selection comprises an operator sequence capable of derepressing a chromosomal operon by repressor titration.

3. The plasmid of claim 2, wherein said region which regulates plasmid copy number, said operator sequence, and said linker region are positioned 5' to 3' in the order: region which regulates plasmid copy number, linker region, operator sequence.

4. The plasmid of claim 2, wherein said region which regulates plasmid copy number, said operator sequence, and said linker region are positioned 5' to 3' in the order: region which regulates plasmid copy number, operator sequence, linker region.

5. The plasmid of claim 2, wherein said plasmid further comprises a region comprising a transcriptional terminator element, wherein said region which regulates plasmid copy number, said linker region, and said region comprising a transcriptional terminator element are positioned 5' to 3' in the order: region which regulates plasmid copy number, linker region, region comprising a transcriptional terminator element.

6. The plasmid of claim 2, further comprising a plurality of operator sequences.

7. The plasmid of claim 6, wherein at least one operator sequence of said plurality of operator sequences is in each of two positions, such that said region which regulates plasmid copy number, said linker region, and said plurality of operator sequences are positioned 5' to 3' in the order: operator sequence, region which regulates plasmid copy number, operator sequence, linker region.

8. The plasmid of claim 5, further comprising
   (a) a partitioning locus which helps ensure that at least one copy of said plasmid is transmitted to each new cell during cell division; and
   (b) a multimer resolution locus which promotes plasmid monomerization.

9. The plasmid of claim 5, wherein
   (a) said origin of replication of said region which regulates plasmid copy number is from the plasmid pMM1,
   (b) said multicloning site is the polylinker sequence from pBluescript KS+, and
   (c) said transcriptional terminator sequence is rrnBT$_1$T$_2$.

10. A plasmid for delivery and expression of a gene in a human cell, comprising:
    (a) a region which regulates plasmid copy number, wherein said region includes an origin of replication sequence;
    (b) a linker region, wherein said linker region includes a multicloning site for inserting said gene;
    (c) a said gene; and
    (d) an element providing selection of a host cell containing said plasmid, wherein said selection does not require a transcribed selection gene on said plasmid.

11. The plasmid of claim 10, wherein said plasmid does not contain an antibiotic resistance gene.

12. The plasmid of claim 10, wherein said element providing selection comprises an operator sequence capable of derepressing a chromosomal operon by repressor titration.

13. The plasmid of claim 10, wherein said plasmid is able to replicate to high copy number in a prokaryotic cell.

14. The plasmid of claim 10, further comprising a region comprising a transcriptional terminator element and at least one nucleic acid restriction site;
    wherein said region which regulates plasmid copy number, said linker region, and said region comprising a transcriptional terminator element are positioned 5'-3' in the order: region which regulates plasmid copy number, linker region, region comprising a transcriptional terminator element.

15. The plasmid of claim 14, wherein
    (a) said origin of replication is from the plasmid pMM1,
    (b) said multicloning site is the polylinker sequence from pBluescript KS +, and
    (c) said transcriptional terminator sequence is rrnBT$_1$T$_2$.

16. A system for selection of a cell containing a plasmid, wherein said system comprises:
    (a) a plasmid of any of claims 1 or 10; and
    (b) a cell containing at least one selection gene incorporated into a chromosome of said cell under the control of a chromosomal operon, wherein said operon is capable of derepression by an operator sequence present on said plasmid by repressor titration.

17. The system of claim 16, wherein said selection gene is an antibiotic resistance gene.

18. The system of claim 16, wherein said operator sequence on said plasmid does not specifically bind a repressor naturally found in said cell.

19. A method for preparing plasmids, comprising the steps of:
    (a) transfecting host cells by contacting a population of said cells with a plurality of plasmids, wherein each said plasmid comprises an element which provides selection of cells containing a plurality of said plasmids, and wherein said selection does not require a transcribed gene on said plasmid;
    (b) selecting at least one transfected cell;
    (c) growing said at least one transfected cell to provide a quantity of cells containing said plasmids; and
    (d) purifying said plasmids from said quantity of cells containing said plasmids.

20. The method of claim 19, wherein said selection is carried out in the absence of antibiotic.

21. The method of claim 19, wherein said element allowing selection is an operator sequence able to derepress a chromosomal operon of said transfected cell by repressor titration.

22. The method of claim 21, wherein said operator sequence is not naturally found in said cell.

23. The method of claim 21, wherein said chromosomal operon comprises an antibiotic resistance gene.

24. The method of claim 19, wherein said plurality of plasmids each comprise:
    (a) a region which regulates plasmid copy number, wherein said region includes an origin of replication sequence;
    (b) a linker region, wherein said linker region includes a multicloning site for inserting a nucleic acid sequence; and
    (c) an operator sequence capable of derepressing a chromosomal operon by repressor titration.

25. A method for delivery of a nucleic acid sequence to a cell, wherein said method comprises the step of contacting said cell with a plasmid of any of claims 1 or 10 for sufficient time to transform said cell,
    wherein said plasmid further comprises a said nucleic acid sequence.

26. A method for selection of a host cell containing a plasmid, wherein said method comprises the steps of:
    (a) selecting a plasmid which appropriately transforms a first cell by contacting said first cell with a plasmid for sufficient time to transform said cell,
    wherein said plasmid is a plasmid of any of claims 1 or 10, further comprising an antibiotic resistance nucleic acid sequence and a site for insertion of a nucleic acid sequence;
    (b) removing said antibiotic resistance nucleic acid sequence from said selected plasmid at flanking nucleic acid restriction sequences;
    (c) recircularizing said selected plasmid to provide a selected plasmid lacking said antibiotic resistance nucleic acid sequence;
    (d) contacting a second cell with said selected plasmid lacking said antibiotic resistance nucleic acid sequence for sufficient time to transform said second cell,
    wherein said second cell contains at least one antibiotic resistance gene incorporated into a chromosome of said cell under the control of a chromosomal operon, wherein said operon is capable of derepression by the operator sequence present on said selected plasmid; and
    (e) selecting a transformed second cell resistant to antibiotic.

27. A method for obtaining a selected plasmid lacking an antibiotic resistance nucleic acid sequence, comprising the step of isolating the selected plasmid lacking an antibiotic resistance nucleic acid sequence from the transformed second cell of claim 26.

28. A method for selection of a host cell containing a plasmid, comprising the steps of:
    (a) contacting a cell with a plasmid for sufficient time to transform said cell, wherein said plasmid is a plasmid of any of claims 1 or 10, wherein said plasmid further comprises a site for insertion of a nucleic acid sequence, and wherein said cell contains a chromosomal operon containing at least one antibiotic resistance gene, wherein said operon is capable of derepression by an operator sequence present on said plasmid by repressor titration;

(b) selecting said transformed cells resistant to antibiotic, wherein said transformed cells resistant to antibiotic are said host cells containing a plasmid.

29. A method for obtaining plasmids lacking an antibiotic resistance nucleic acid sequence, comprising the step of isolating the plasmids lacking an antibiotic resistance nucleic acid sequence from the transformed cells of claim 28.

30. A plasmid for delivery of a nucleic acid sequence to a human cell, comprising:

a 5' flanking region which regulates plasmid copy number, wherein said 5' flanking region includes a origin of replication sequence;

a 3' flanking region which regulates selection of plasmid containing cell and is divergently oriented to said 5' flanking region, wherein said 3' flanking region includes a nucleic acid sequence encoding for antibiotic resistance; and a linker region connecting said 5' flanking region to said 3' flanking region, wherein said linker region includes a multicloning site element for inserting a nucleic acid cassette, and a transcriptional terminator element to ensure transcription of said antibiotic resistance sequence does not transcribe through said nucleic acid cassette.

* * * * *